(12) United States Patent
Nagarkar et al.

(10) Patent No.: US 7,486,766 B1
(45) Date of Patent: *Feb. 3, 2009

(54) MICRO CT SCANNERS INCORPORATING INTERNAL GAIN CHARGE-COUPLED DEVICES

(75) Inventors: Vivek V Nagarkar, Newton, MA (US); Sameer V Tipnis, Waltham, MA (US)

(73) Assignee: Radiation Monitoring Devices, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/037,018

(22) Filed: Feb. 25, 2008

Related U.S. Application Data

(63) Continuation of application No. 11/158,918, filed on Jun. 21, 2005, now Pat. No. 7,352,840.

(60) Provisional application No. 60/581,478, filed on Jun. 21, 2004.

(51) Int. Cl.
*A61B 6/03* (2006.01)
(52) U.S. Cl. .......................... 378/19; 378/43
(58) Field of Classification Search .............. 378/4, 378/19, 43
See application file for complete search history.

(56) References Cited

U.S. PATENT DOCUMENTS

| | | | | |
|---|---|---|---|---|
| 4,190,773 A | * | 2/1980 | Braden et al. | 378/10 |
| 4,607,380 A | * | 8/1986 | Oliver | 378/138 |
| 5,153,438 A | * | 10/1992 | Kingsley et al. | 250/370.09 |
| 5,155,365 A | * | 10/1992 | Cann et al. | 250/363.02 |
| 5,376,795 A | * | 12/1994 | Hasegawa et al. | 250/363.04 |
| 5,391,877 A | * | 2/1995 | Marks | 250/363.04 |
| 5,391,879 A | * | 2/1995 | Tran et al. | 250/367 |
| 5,412,705 A | * | 5/1995 | Snoeren et al. | 378/98.3 |
| 5,463,666 A | * | 10/1995 | Eberhard et al. | 378/4 |
| 5,465,283 A | * | 11/1995 | Tam | 378/4 |
| 5,591,977 A | * | 1/1997 | Green et al. | 250/363.03 |
| 5,864,146 A | * | 1/1999 | Karellas | 250/581 |
| 5,936,247 A | * | 8/1999 | Lange et al. | 250/363.03 |
| 6,205,347 B1 | * | 3/2001 | Morgan et al. | 600/407 |
| 6,399,951 B1 | * | 6/2002 | Paulus et al. | 250/370.13 |
| 6,448,559 B1 | * | 9/2002 | Saoudi et al. | 250/367 |
| 6,449,331 B1 | * | 9/2002 | Nutt et al. | 378/19 |

(Continued)

FOREIGN PATENT DOCUMENTS

JP  11231056 A  *  8/1999

(Continued)

OTHER PUBLICATIONS

Miller, et al., "Single-photon spatial and energy resolution enhancement of a columnar CsI(Tl)/EMCCD gamma-camera using maximum-likelihood estimation," Manuscript, 10 pages (2006).*

(Continued)

*Primary Examiner*—Chih-Cheng G Kao
(74) *Attorney, Agent, or Firm*—Townsend and Townsend and Crew LLP

(57) ABSTRACT

The present invention provides internal gain charge coupled devices (CCD) and CT scanners that incorporate an internal gain CCD. A combined positron emission tomography and CT scanner is also provided.

17 Claims, 15 Drawing Sheets

U.S. PATENT DOCUMENTS

| | | | | |
|---|---|---|---|---|
| 6,483,892 | B1 * | 11/2002 | Wang et al. | 378/43 |
| 6,670,614 | B1 * | 12/2003 | Plut et al. | 250/363.04 |
| 2002/0031203 | A1 * | 3/2002 | Polichar et al. | 378/98.2 |
| 2003/0058984 | A1 * | 3/2003 | Susami et al. | 378/19 |
| 2005/0226361 | A1 * | 10/2005 | Zhou et al. | 378/4 |

FOREIGN PATENT DOCUMENTS

WO     WO 200075691 A1 * 12/2000

OTHER PUBLICATIONS

Nagarkar, V., et al., "A CCD-based detector for SPECT," Manuscript, 4 pages (Oct. 19, 2004).*

Nagarkar, V., et al., "Microcolumnar Csl(TI) films for small animal SPECT," Manuscript, pp. 1-4 (Oct. 18, 2004).*

Teo, B.K., et al., "Evaluation of a EMCCD detector for emission-transmission computed tomography," IEEE, pp. 3050-3054 (2005).*

Feldkamp et al., "Practical cone-beam algorithm," J. Opt. Soc. Am., 1:612-619 (1984).*

Flannery et al., "Observational strategies for three-dimensional synchrotron mlcrotomography," J. Appl. Phys., 62:4668-4674 (1987).*

Flannery et al., "Three-Dimensional X-ray Microtomography," Science, 237:1439-1444 (1997).*

Fujita et al., "A simple method for determining the modulation transfer function in digital radiography," IEEE Trans. Med. Imaging MI, 11:34-39 (1992).*

Liu, H et al., "Methods to calculate the lens efficiency in optically coupled CCD x-ray imaging systems," Med. Phys., 21:1193-1195 (Jul. 1994).*

Maidment and Yaffe, "Analysis of signal propagation in optically coupled detectors for digital marnmography: II. Lens and fibre optics," Phys. Med. Biol., 41:475-493 (1996).*

Paulus et al., "A new X-ray computed tomography system for laboratory mouse imaging," IEEE Trans. Nucl. Sci., 46:558-564 (1999).*

Paulus et al., "High resolution X-ray computed tomography: an emerging tool for small animal cancer research," Neoplasia, 2:62-70 (Jan.-Apr. 2000).*

Vedantham et al., "Full breast digital mammography with an amorphous silicon-based flat panel detector: physical characteristics of a clinical prototype," Med. Phys., 27:558-567 (Mar. 2000).*

Vedantham et al., "Mammographic Imaging with a small format CCD-based digital cassette: physical characteristics of a clinical system," Med. Phys., 27:1832-1840 (Aug. 2000).*

Yu and Boone, "Lens coupling efficiency: derivation and application under differing geometrical assumptions," Med. Phys., 24:565-570 (Apr. 1997).*

Nagarkar et al., Structured CsI(TI) scintillators for X-ray imaging applications, IEEE Transactions on Nuclear Science, (Jun. 1998), vol. 45, Issue 3, Part 1, pp. 492-496.*

Goertzen et al., Simultaneous molecular and anatomical imaging of the mouse in vivo, Physics in Medicine and Biology, (Dec. 2002), vol. 47, Issue 24, pp. 4315-4328.*

Machine Translation of JP 11-231056 A, which was published in (Aug. 1999).*

Photometrics, Cascade: 512F, (Apr. 7, 2003), Rev B2.*

Photometrics, Cascade: 512F, (2004), Rev C0.*

Nagarkar et al., A High Speed Functional MicroCT Detector for Small Animal Studies, Nuclear Science Symposium Conference Record, 2004 IEEE, (Oct. 16-22, 2004), vol. 5, pp. 3229-3233.*

* cited by examiner

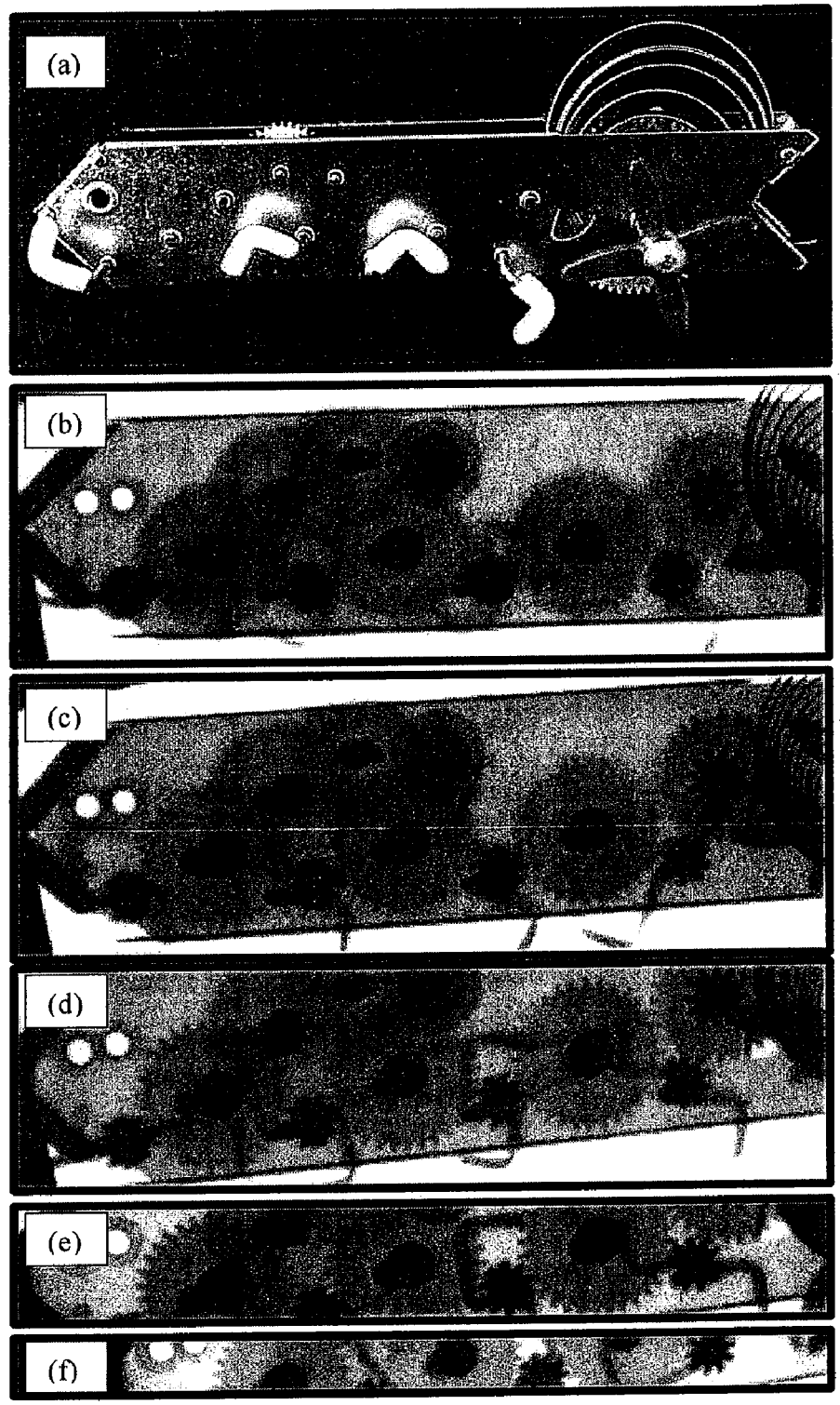
FIGS. 13(a) to (f)

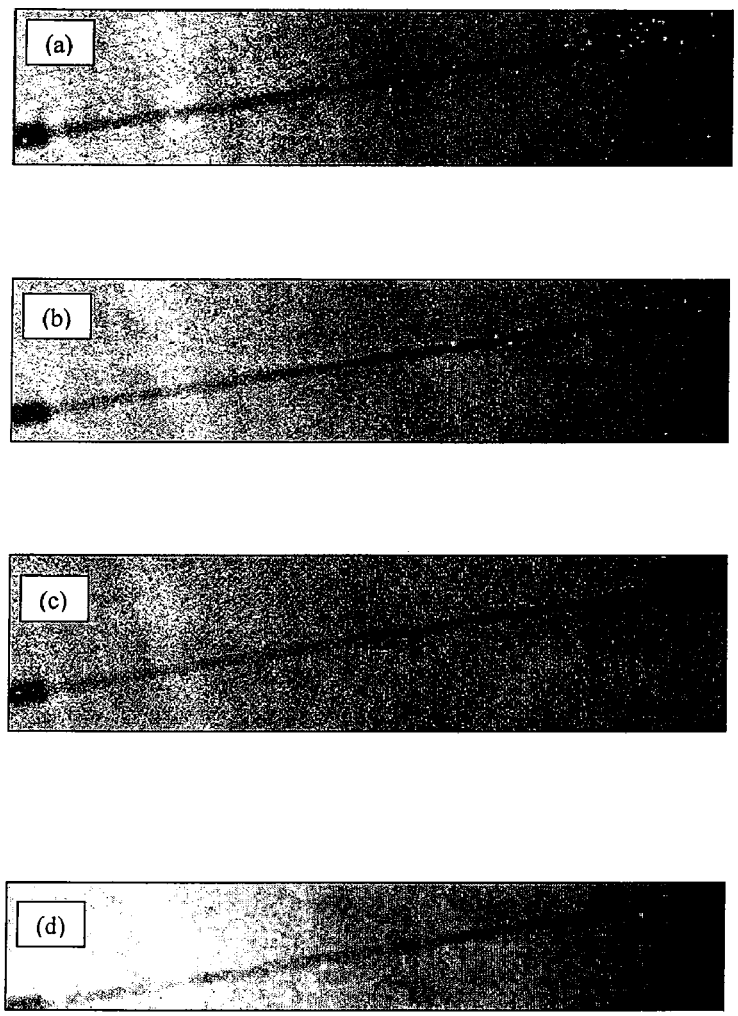
FIGS. 14(a) to (d)
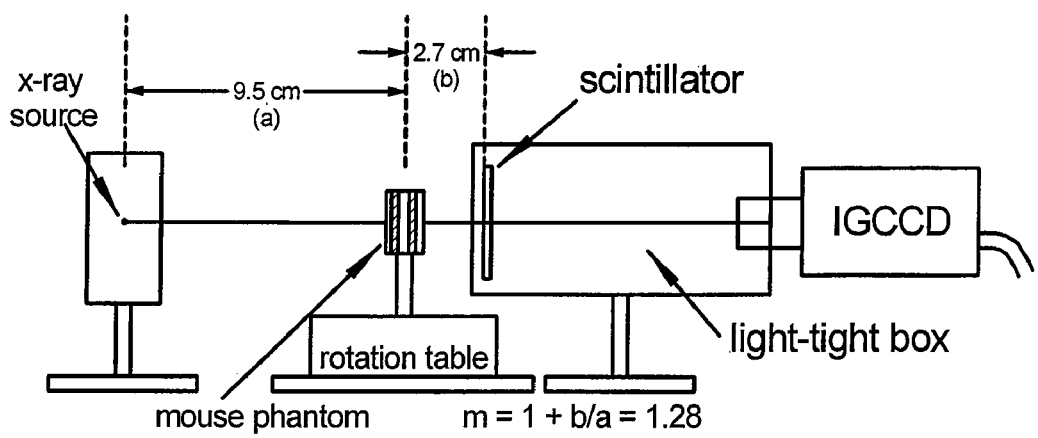
FIG. 15(a)

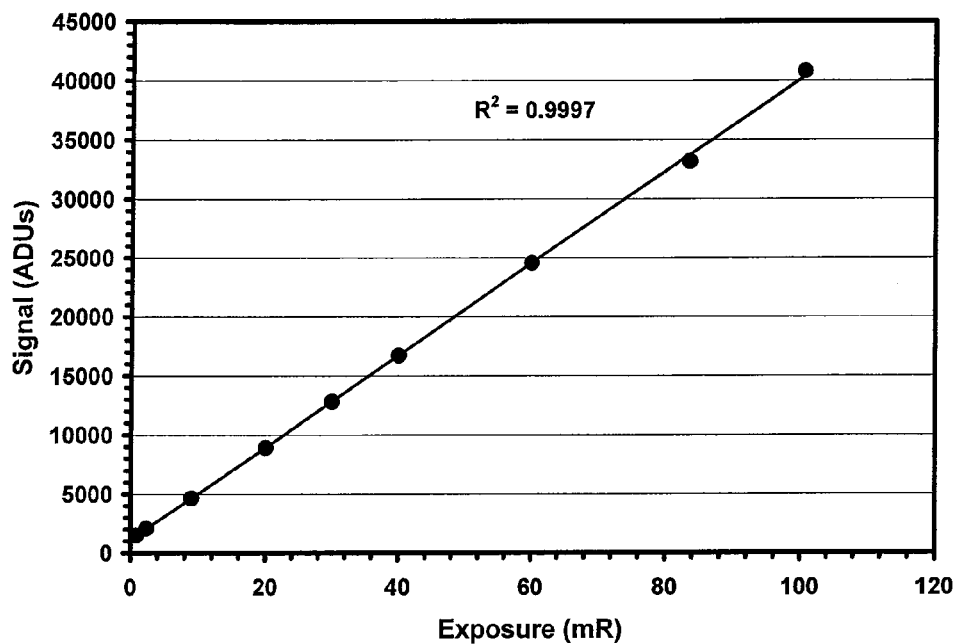
FIG. 18
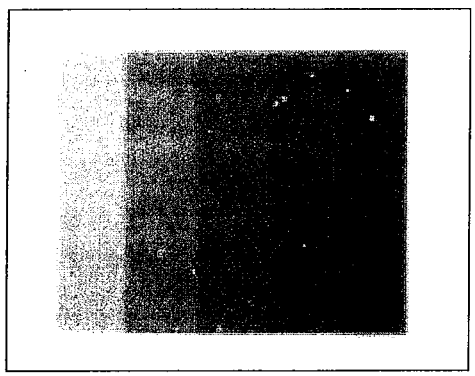
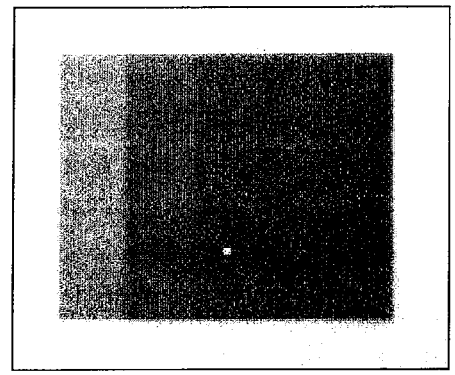
FIG. 19A          FIG. 19B

MICRO CT SCANNERS INCORPORATING INTERNAL GAIN CHARGE-COUPLED DEVICES

CROSS REFERENCE TO RELATED APPLICATIONS

The present invention is a continuation of U.S. patent application Ser. No. 11/158,918, filed Jun. 21, 2005, which claims benefit to U.S. provisional patent application Ser. No. 60/581,478, filed Jun. 21, 2004, and is related to and claims priority to commonly owned provisional patent application entitled "Combined Radionuclide and X-Ray Imaging Device," Ser. No. 60/581,400, filed Jun. 21, 2004, and its non-provisional U.S. patent application Ser. No. 11/158,938, filed Jun. 21, 2005, the complete disclosures of which are incorporated herein by reference.

STATEMENT AS TO RIGHTS TO INVENTIONS MADE UNDER FEDERALLY SPONSORED RESEARCH AND DEVELOPMENT

This work was supported by grant number 1 R43 CA0187-01 from the National Institutes of Health. The United States Government may have certain rights in the invention.

BACKGROUND OF THE INVENTION

The present invention relates generally to imaging systems. More specifically the present invention relates to novel micro-CT scanners that incorporate internal gain charge-coupled devices (CCD). Further, a combined positron emission tomography (PET)/CT imaging system is also provided.

Dedicated high-resolution small animal imaging systems have recently emerged as important new tools for cancer research. These systems permit noninvasive screening of animals for mutations or pathologies and to monitor disease progression and response to therapy. Among these, x-ray microcomputed tomography (microCT), shows promise as a cost-effective means for detecting and characterizing soft tissue structures, skeletal abnormalities, and tumors in live animals (Paulus et al., *IEEE Trans. Nucl. Sci.* 46:558-564 (1999); Paulus et al., *Neoplasia* 2:62-70 (2000)). Current CT systems provide high-resolution images with excellent sensitivity to skeletal tissue and good sensitivity to soft tissue, particularly when contrast-enhancing media are employed. However, use of this powerful modality for functional studies such as those of tumor vascular physiology or involving true whole organ physiologic imaging is difficult due to the lack of a suitable x-ray imaging detector. Typically, such studies require a detector that can simultaneously provide high speed, high sensitivity, and a large active imaging area.

In 1987 Flannery et al. (Flannery et al., *Science* 237:1439-1444 (1997); Flannery et al., *J. Appl. Phys.* 62:4668-4674 (1987)) brought x-ray microtomography into a new era with the introduction of a three-dimensional imaging system using a two-dimensional detector comprising of a phosphor plate optically coupled to a charge-coupled device (CCD) array. This, coupled with the development of a new three-dimensional "cone-beam" image reconstruction algorithm (Feldkamp et al., *J. Opt. Soc. Am.* 1:612-619 (1984)), spurred the development of a large number of microtomography systems for high-resolution specimen analysis in the 1990s. The majority of the studies performed using these instruments focused on high-density tissue such as bone or teeth for which magnetic resonance imaging is less successful. For in vivo small animal studies, particularly large population studies, these systems become cumbersome to operate because the subject must be confined in a rotating carrier designed to prevent soft-tissue organ motion. Recently, dedicated small animal microCT scanners have been developed in which the detector and x-ray source rotate about a fixed "patient bed" much like clinical CT systems. A table of the currently available micro-CT systems from various manufacturers is included below.

TABLE I

Some of the major small animal micro-CT systems and the manufacturers currently in market.

| Manufacturer | Model | X-ray Source | X-ray Detector | Max. object size | Reconstruction Resolution | Main application |
|---|---|---|---|---|---|---|
| SKYSCAN | 1072 (high-resolution/Cone-beam scanner) | μ-focus, 5 μm (4W)/8 μm (8W), 0-100 kV, 0-250 μA | 1024 × 1024 12-bit cooled CCD, 3.7:1 fiberoptic taper coupled to scintillator (2) 768 × 512 8 bit CCD, lens coupled to scintillator | 20 mm @ 1K × 1K, 37 mm @ 2K × 2K (2) 20-50 mm @ 1K × 1K | | Electronic components, biomedical objects, composites etc. |
| | 1074 (portable/Cone-beam scanner) | 20-40 kV/0-1000 μA | 768 × 576 8-bit, lens-coupled to scintillator | 16-30 mm | 40 μm or 22 μm | Metal foams, plastics, composites, biomedical objects |
| | 1076 (high-resolution/Cone-beam scanner) | μ-focus, 20-100 kv, 10W, 5 μm (4W) | 4000 × 2300 12-bit cooled with fiberoptic coupled to scintillator | 68 or 35 mm Φ, 200 mm long | 1000 × 1000 to 8000 × 8000, 9 μm/18 μm/35 μm | In-vivo small animal imaging |
| | 1078 (high-speed/Cone-beam scanner) | 2 tubes, 20-65 kV each, 40 W each | 1280 × 1024 12-bit | 48 mm Φ, 140 mm long | 512 × 512 × 512 @ 94 μm or 1024 × 1024 × 1024 @ 47 μm | High-throughput in-vitro/in-vivo small animal imaging |

TABLE I-continued

Some of the major small animal micro-CT systems and the manufacturers currently in market.

| Manufacturer | Model | X-ray Source | X-ray Detector | Max. object size | Reconstruction Resolution | Main application |
|---|---|---|---|---|---|---|
| SCANCO Medical | μ-CT 20 (high-resolution/ Fanbeam) | μ-focus 5-7 μm, 50 kVp/32 keV(160 μA) | | Max. FOV = 17.4 mm, 50 mm long | 512 × 512 or 1024 × 1024, slice: 25-35 μm | Biomedical objects |
| | μ-CT 40 (high-resolution/ Cone-beam) | μ-focus 5-7 μm, 30-70 kVp/20-50 keV(160 μA) | 2048 × 256, 24 μm pitch | FOV = 12-37 mm, 80 mm long | 512 × 512 or 1024 × 1024 or 2048 × 2048, 6-72 μm isotropic | Biomedical objects, small animal imaging |
| | μ-CT 80 (high-resolution/ large samples/ Cone-beam) | μ-focus 5-7 μm, 30-70 kVp/20-50 keV(160 μA) | 2048 × 128, 48 μm pitch | FOV = 76 mm, 120 mm long | 512 × 512 or 1024 × 1024 or 2048 × 2048, 10-74 μm nominal isotropic | Biomedical objects, small animal imaging |
| | Viva-CT 40 (high-speed) | μ-focus 5-7 μm, 30-70 kVp/20-50 keV(160 μA) | 2048 × 252, 26 μm pitch | FOV = 20-38 mm, 145 mm long | 512 × 512 or 1024 × 1024 or 2048 × 2048, 10-72 μm nominal isotropic | Biomedical objects, small animal imaging |
| GE Medical Systems | MS μ-CT (cone-beam) | μ-focus, 20-90 kVp, 0.18 mA (max.) | 70 mm × 70 mm area, 2048 × 2048 pixel CCD | Max. Φ = 40 mm | 10-100 μm | Biomedical objects, tissue specimens |
| | RS μ-CT (cone-beam) | 80 kVp, W target | 3500 × 1750 CCD, 10 μm pixels | 90 mm Φ × 45 mm long | 90/45 μm, 1750 × 1750 × 875 | In vivo, in vitro, Volumetric small animal CT |
| ImTek Inc. | MicroCAT II | 80 kVp, 9 μm, W target | Up to 4096 × 4096 CCD, cooled, fiberoptic taper coupled to scintillator | Imaging area up to 110 mm × 110 mm | Image circle from 35 mm to 110 mm Φ | In vivo, Volumetric small animal CT |

While the above systems are capable of mass production of small animal CT systems, at present they do not incorporate high speed CT technology. In particular, most of the conventional systems employ CCD based detector arrays, micro-focus x-ray tubes, and have reconstructed image resolution between 50 and 100 microns. It is important to note that some of the existing microCT systems are not capable of in vivo imaging, while others having this capacity are limited by their speed of operation resulting in data acquisition times of several minutes to hours. Thus, the existing systems cannot be used for high-speed dynamic, i.e., functional, studies, where high sensitivity and high-speed x-ray imaging is required. For example, the fastest scan time among the conventional current high-throughput systems is provided by SkyScan-1078, which is about 49 seconds at 94 μm resolution and 1.44 degree rotational steps (250 views).

Most of the current microCT systems employ CCD based detector arrays which provide adequate spatial resolution (50 to 100 μm) and imaging area (5 cm×5 cm), but offer limited imaging speeds of 1 to 5 seconds per projection. This translates into volumetric data acquisition times in the range of 5 to 30 minutes for high resolution imaging, making it impossible to use them for functional studies. As microCT devices are not yet capable of functional imaging, important functional and physiologic studies in animal models of various diseases such as solid tumors, stroke physiology, and acute myocardial ischemia, are performed using existing clinical CT scanners. The clinical CT scanners can provide the required temporal resolution, but offer a tradeoff between spatial resolution and imaging volume. For example, the GE LightSpeed multi-slice CT scanner can provide 2 cm image coverage with a 0.5 cm (500 μm) slice thickness or a 0.5 cm image coverage with a 0.125 cm (125 μm) slice thickness, and a 300×300 μm nominal, in plane resolution. Even though the existing clinical scanners are capable of cine-mode data acquisition, only from a limited volume. For example, a 2 cm-long volume can be studied if a slice thickness of 5 mm is used. Also, the minimum slice thickness is limited to 1.25 mm, and in this mode only 5 mm of the volume is covered.

Additional difficulties arise from the fact that the image voxels are anisotropic, which lead to severe partial volume artifacts in small animal imaging, where each voxel represents a heterogeneous sample of various tissue components and the calculated physiologic parameters represent an average physiological behavior at best. Thus, the limited spatial resolution and small volume coverage associated with the current CT scanners are suboptimal for small animal functional studies related to accurate characterization of tissue-specific physiology. Isotropic dynamic perfusion studies and whole organ physiologic imaging, require detectors with 100 to 300 frames per second readout, spatial resolution of ~100 μm, and a x-ray detection efficiency of >85%. Such an imaging system allows a repeated volumetric data acquisitions in seconds.

The limitations of current CCD based microCT x-ray imaging systems arise from two factors. First, readout speeds are curtailed in order to minimize the system read noise, which increases with the readout rates. An increased read noise reduces the signal to noise ratio (SNR) and the effective dynamic range of the detector. Recently developed CCD based x-ray imaging systems address the speed issue to some extent, however, at the cost of reduced SNR, pixel resolution, and sensitivity. Second, the CCDs themselves are not used for x-ray detection. Rather, a high density scintillator is placed between the x-ray beam and the CCD, so that the x-rays are stopped in the scintillator, their energy converted to light photons, which are subsequently detected by the CCD. In most systems that typically use $Gd_2O_2S$ (GOS) phosphors, such as the Kodak® MinR-2000, the sensitivity is limited due to the tradeoff between x-ray stopping power and spatial resolution. Thicker GOS screens improve sensitivity, but reduce the spatial resolution because the light photons spread from the conversion point, and scatter as well. Thus, there is a need for improved speed, spatial resolution and SNR. At present important functional, physiologic studies of various diseases such as solid tumors, stroke physiology, and acute myocardial ischemia in small animal models are performed using clinical CT scanners. This is due to the fact that microCT devices are not yet capable of the high processing speeds and resolution necessary for functional imaging.

The development of high-speed microCT systems allows for the use of CT for functional imaging, substantially enhancing the role of this powerful technique, which is already well established for anatomical imaging. Functional micro-CT provides a novel approach for longitudinal high-resolution investigations of, for example, new anti-angiogenic therapies by using perfusion imaging of a tumor. Moreover, investigations of stroke physiology and developing new therapeutic approaches for treatment of acute cerebral ischemia will largely benefit from the availability of a high resolution imaging modality with enough active imaging area to cover the whole organ of interest. This approach will substantially improve the accuracy of the quantification of physiologic parameters, such as blood flow (BF), blood volume (BV), transcapillary transfer constants (K1, k2), extraction fraction (E) and permeability surface area product (PS).

In addition to the tissue specific physiology studies, functional CT techniques are also being used for experimental studies of solid tumor vascular physiology and angiogenesis, and its inhibition by anti-angiogenic therapies in mice. Additionally, studies of cerebrovascular physiology in experimental stroke models in rats, rabbits, and monkeys, and investigations of myocardial ischemia are in progress. In all such functional CT studies a short bolus of radio-opaque contrast agent is administered and its first passage, which takes only a few seconds, is recorded through the region of interest. Several images have to be acquired at closely spaced time intervals in order to apply tracer kinetic modeling to these temporal data for quantification of physiologic parameters.

Transgenic and "knock-out" mice have provided important insights into the genetic mechanisms underlying atherosclerosis, hypertension, and diabetes. However, similar advances in the field of myocardial infarction (MI) have been impeded by the challenge of performing coronary ligation during survival surgery in animals weighing 30 g or less. Nevertheless, this challenge has been overcome in recent years and numerous studies now demonstrate the feasibility of inducing MI in intact mice. Thus the surgical challenge has now given way to the technical challenge of assessing myocardial infarction, left ventricular dimensions, and cardiac function in very small animals with high heart rates (>500 bpm). Although it is possible to non-invasively assess myocardial perfusion and infarction in patients with radionuclide techniques, the limited spatial and temporal resolution of, for example, Single Photon Emission Computed Tomography (SPECT), effectively precludes its application in mice. However, more accurate measurements can be made through the use of cardiac magnetic resonance imaging (MRI), which has emerged as one of the most powerful modalities currently available for the noninvasive assessment of ischemic heart disease.

Although the utility of MRI for imaging cardiac structure, function, and infarct size in mice has been well established, there are several disadvantages with MRI that limit its widespread application in biomedical research. First, a high cost associated with high field strength (e.g., $\geqq 4.7$ T) MRI imaging limits its accessibility to researchers. Second, the high field strength magnets preclude the use of any metallic objects in or on the animal or as part of support equipment. Third, the overall time for setup and imaging small animals with MRI can be quite lengthy. Finally, due to the high heart rates in small animal models, particularly mice (>500 BPM), cardiac MRI does not provide the required temporal resolution to capture the first-pass of a contrast agent in order to obtain the input function that would allow the assessment of myocardial perfusion in the mouse. A high temporal resolution CT system is expected to allow simultaneous assessment of myocardial perfusion and function in the mouse heart. The ability to correlate flow and function is of great importance in cardiovascular research which cannot be performed using MRI. In addition to cardiac functional analysis, there are novel applications, such as liposomal CT contrast agents, for assessing myocardial perfusion and risk area in the murine heart. The advantage of the liposomal contrast agent over the standard contrast agents that are usually employed with CT or MR imaging is that the liposomal agent remains trapped intravascularly allowing accurate assessment of myocardial perfusion and risk area.

Over the recent years, researchers have been combining data from various modalities such as, for example, positron emission tomography (PET) and MRI to provide complementary data for diagnosis. Similarly, there is a significant interest in combining image data from microPET and microCT, and combining the modalities of SPECT and CT.

BRIEF SUMMARY OF THE INVENTION

The present invention relates to a microCT system that comprises an x-ray detector that is capable of imaging at a rate of up to 300 frames per second (fps). The present invention also provides an x-ray generator that better takes advantage of the improved imaging capabilities made possible by the x-ray detector of the present invention.

The CT systems of the present invention allow for volumetric CT imaging of small animals in seconds compared to several minutes needed for the conventional CT systems. The systems of the present invention have considerable potential as a research tool for dynamic studies, particularly for the study of physiology in small animals, and in other important applications in medical imaging.

In one embodiment, the CT systems of the present invention comprise an x-ray detector that is based on an internal gain CCD ("IGCCD") coupled to a high sensitivity, high-resolution microcolumnar CsI(Tl) scintillator via a fast lens.

Such CCDs combine the high resolution and low noise of a CCD, and the internal gain of an avalanche photo diode (APD). The presence of an internal gain effectively reduces the read noise even when operated at high frame rates of 300 fps, thus improving the image signal-to-noise ratio (SNR).

The microcolumnar CsI(Tl) scintillator converts incident x-rays into visible light with very high efficiency and, by virtue of its structure channels the light towards the CCD. This minimizes the traditional tradeoff between spatial resolution and detection efficiency. Furthermore, with its fast scintillation decay, the CsI(Tl) allows rapid x-ray imaging without image blurring arising from residual intensity from previous exposures. Thus, the combination of a microcolumnar CsI(Tl) scintillator and an internal gain CCD can provide very high sensitivity, for example with a range of about 90% to about 98%, high spatial resolution, such as for example, from about 50 to about 70 μm, and a substantially improved SNR, such as, for example an improvement of about 10 times over currently available units.

The x-ray detectors of the present invention typically comprise a large active area and have a high speed of operation permitting high-speed data acquisition through a whole organ, such as the brain, thus enabling construction of temporal curves of the contrast passage for each individual voxel.

For a further understanding of the nature and advantages of the invention, reference should be made to the following description taken in conjunction with the accompanying drawings.

BRIEF DESCRIPTION OF THE DRAWINGS

FIGS. 13(a)-13(f) illustrate dynamic images (unprocessed) of a toy phantom—13(a) the toy, 13(b) at 30 fps, 13(c) at 50 fps, 13(d) at 90 fps, 13(e) 120 fps, and 13(f) at 225 fps. The gears in the toy are made from plastic and metal, and depending on their diameter are moving at a speed of up to 120 rpm.

FIGS. 14(a)-14(d) illustrate dynamic images (unprocessed) of a contrast agent (iodine) in a glass capillary: 14(a) at 30 fps, 14(b) at 50 fps, 14(c) at 90 fps, 14(d) at 120 fps. The contrast agent was moving from the right on the image to the left. The leading edge of the iodine is approximately in the middle of the capillary in each image.

FIGS. 15(a) and 15(b) illustrates an experimental CT setup used for imaging studies.

FIG. 18 illustrates the response uniformity of the detector.

FIGS. 19(a) and 19(b) illustrate images of a contrast phantom obtained using the disclosed x-ray detector. FIG. 19(a) 16 mR image. FIG. 19(b) 1 mR image.

DETAILED DESCRIPTION OF THE INVENTION

Figure 1:
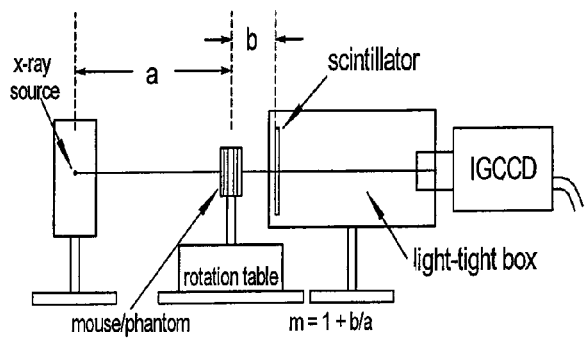
FIG. 1 schematically illustrates a high speed CT scanner that comprises an x-ray detector of the present invention. The CT scanner system generally comprises a source of penetrating radiation (e.g., x-ray source—typically an x-ray tube), a detector assembly, associated processing electronics, and a computer and software for image reconstruction, display, manipulation, post-acquisition calculations, storage and retrieval.

FIG. 1 schematically illustrates a high speed CT scanner system that is encompassed by the present invention. The CT scanner system generally comprises a source of penetrating radiation (e.g., x-ray source—typically an x-ray tube), an assembly for either rotating the x-ray source around the subject or for rotating the subject; a detector assembly; associated processing electronics; and a computer and software for image reconstruction, display, manipulation, post-acquisition calculations, storage and retrieval. The detectors may either be stationary or the detectors may be rotating. Alternatively, the CT system may include means to rotate a subject placed within the imaging volume and the CT assembly would then remain fixed in space.

The detector assembly can vary in the detection principles. For instance, some CT scanners have used gas detectors, where x-rays are converted to ionization electrons and positive ions in the gas, which then drift and are collected at electrodes to which an appropriate voltage has been applied. Similarly, the detection process can be mirrored in a solid state detector. Conventional CT scanners often use a two-step detection scheme, wherein x-ray photons are stopped by a scintillator, and the scintillator produces much lower energy photons, mostly in the visible range. These photons are then detected by a suitably placed detector.

To better understand the source of the improvements over the conventional CT systems resulting from the present invention, each novel component of the present CT system will be discussed separately. As can be appreciated by those of ordinary skill in the art, the present invention can use the same x-ray source, computer, software, and rotation assembly as existing CT scanners. This is advantageous in enhancing the value of the present invention by making it easier to incorporate the novel elements into existing CT systems. The present invention involves all aspects of the detector assembly and processing electronics, specifically, the combination of a scintillator, light coupling scheme, and light detector.

Although the x-ray source does not necessarily have to be different, the added capability of the described detector assembly makes it advantageous to also augment the capabilities of the x-ray source. Modifications of the x-ray source made possible by the improvements in detector sensitivity made possible by the present invention are also described further herein.

Scintillator

The scintillators of the present invention used in high-speed imaging applications, by intrinsic nature of the problem are inherently light-starved. The problem is exacerbated when the source of light is the passive output of an x-ray scintillator screen. Thus, in such applications a premium is placed on the x-ray to light conversion efficiency, the speed of emission or decay time, and the x-ray stopping power of the scintillator. CsI(Tl) has high light conversion efficiency, a fast decay time, good x-ray stopping properties, and is easily fabricated. Table II lists the material's scintillation properties. In one configuration, the CsI(Tl) material is vapor deposited on a fiberoptic/graphite substrate to form a high resolution microcolumnar screen.

Following their deposition, microcolumnar CsI(Tl) films can be coated with reflective layer(s), such as for example, $Al_2O_3$, aluminum, white paint, and the like, and a moisture protective barrier, such as for example SiO and $Si_3N_4$, ZrO and $SiO_2$, and the like. Where films are deposited on an amorphous carbon substrate, only a moisture protective layer may be deposited. To achieve highly reflective coat, 250 nm thick three and one half to five and one half bi layers of SiO and $Si_3N_4$ ($n_{SiO}$=1.4 and $n_{Si3N4}$=1.6 to 2.1) can be formed. The order and thickness of each of these layers can be tailored to alter reflection/transmission properties of the coatings. Similarly, coatings of ZrO ($n_{ZrO}$=2.3) and $SiO_2$ ($n_{SiO2}$=1.5) can be used. These can be formed using a plasma enhanced chemical vapor deposition (PECVD) technique.

In an embodiment comprising a fiberoptic based CsI(Tl) screen, a polymer-metal bi-layer combination can also be considered. A thin polymer layer can be formed on the relatively rough CsI(Tl) film surface (arising from needle shaped micro-columns) to improve the film 'flatness,' which is known to affect the reflective properties of coatings. Subsequently, a high reflectance metal layer, such as, for example, aluminum can be deposited using e-beam evaporation.

In embodiments of the present invention comprising an amorphous carbon based screen, the CsI(Tl) side can be

TABLE II

Properties of CsI(Tl) important for high-speed imaging

| Scintillator Material | Screen Form | Decay Time (ns) | Afterglow | Conversion Efficiency (Ph/Mev) | Wavelength of Peak Emission (nm) | CCD QE (%) Front Ill. | Material Density (g/cc) |
|---|---|---|---|---|---|---|---|
| CsI(Tl) | Columnar | 680 | Yes | 61,000 | 540 | 35 | 4.51 |

One embodiment of the present invention involves vapor-deposition of CsI(Tl) on a fiberoptic faceplate and a low cost graphite substrate. The black surface of the substrate material minimizes optical scatter at the CsI-carbon interface, thereby improving the spatial resolution. Due to its black color, amorphous carbon substrates reduce the total light output, but provide an excellent spatial resolution. A reflective substrate may be formed by vapor deposition of a high reflectance material such as, for example, aluminum or $TiO_2$ on graphite prior to CsI(Tl) deposition. The fiberoptic faceplates with 6 μm fibers and interstitial extramural absorption fibers (EMA) can be obtained from sources such as Incom, Inc., Southbridge, Mass. The substrates can be subjected to plasma cleaning procedures to ensure good film adhesion. Currently, it is possible to produce up to 10×10 cm², up to 500+μm thick screens. As a scanner may be used for x-ray energies ranging from 30 kVp to 65 kVp, films of various thickness in the range of 100 μm to 500 μm can be deposited to ensure >80% absorption of x-rays. A specially designed planetary system may be used to obtain better than 0.3% thickness non-uniformity. Care should be exercised to maintain the Tl activator concentration in the evaporated films as this can effect light output properties of the resulting screens as set forth below.

An important parameter to control is the Tl activator concentration in vapor deposited films. This is accomplished by co-evaporating Tl with CsI. For high light yield, higher Tl concentration of 0.5 to 0.7 mole % can be used. For high resolution, a moderate 0.2 to 0.3 mole % Tl can be incorporated in the films. Resulting films can be annealed to ensure response uniformity over the entire film area.

coupled to the CCD. After deposition of CsI(Tl) a transparent protective hard coat of Aluminum Oxide can be formed using plasma enhanced deposition process. During this process, substrates are maintained at room temperature to prevent damage to the CsI(Tl). It is estimated that the hard coat layer thickness can vary between about 500 nm to about 1.5 μm.

Coating technologies have been well researched and there are numerous ways of forming coatings with required optical and/or protective properties required for the present invention.

Figure 2A:
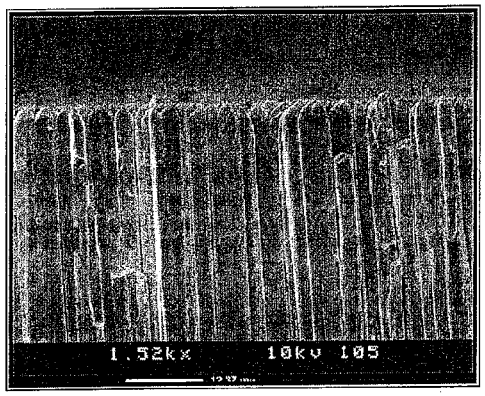
FIG. 2(a) depict a SEM micrograph of a 230 μm thick microcolumnar CsI(Tl) film showing 2 μm to 5 μm diameter columns.
Figure 2B:
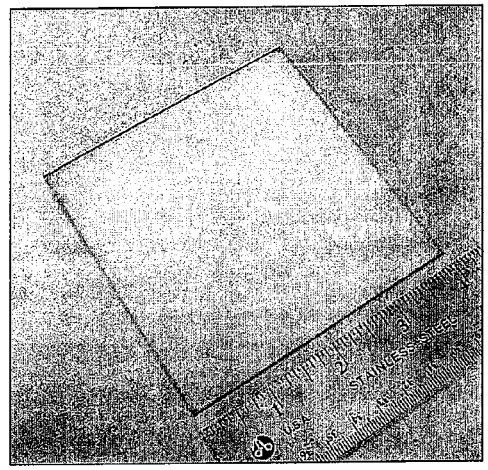
FIG. 2(b) is a photograph of a 10×10 cm$^2$ CsI(Tl) film deposited on an amorphous carbon substrate.

FIG. 2(a) is an SEM micrograph of one representative microcolumnar CsI(Tl) film showing excellent columnar structure. The illustrated microcolumnar CsI(Tl) film is about 230 μm thick and has columns that have a diameter between about 2 μm and about 5 μm. In other embodiments screens of about 150 μm thick (high resolution screens; 76% attenuation at 40 keV) and about 400 μm thick (high efficiency screens; 97% attenuation at 40 keV) have also been made. The columnar structure allows fabrication of thick films to enhance the x-ray absorption while minimizing the lateral light spread within the screen, thereby maintaining an excellent spatial resolution. This structure, therefore, overcomes the traditional tradeoff between spatial resolution and detection efficiency. After deposition, the films were coated with a thin layer of optically clear, low index of refraction, protective material, such as for example, SiO, $Si_3N_4$, ZrO and $SiO_2$. This layer provided both, the protection from atmospheric moisture and from scratching the surface during normal handling. FIG. 2(b) illustrates a 10×10 cm² CsI(Tl) film deposited on an amorphous carbon substrate.

Referring now to Table III, of the materials outlined, GOS (Tb) and GOS(Pr) are commercially available in the form of screens with a mass thickness of about 30 to 150 mg/cm$^2$ which provide an adequate detection efficiency for the present invention. Materials such as YAG and CaWO$_4$ are available as powders, but not in screen form, which is then fabricated using a standard slurry technique. Fabrication involves forming a slurry using 95% scintillator powder and 5% binder compound, which is then coated on a reflective surface. The resulting screens can be laminated for protection. Each of the powdered screens and the microcolumnar CsI(Tl) screen were subjected to detailed characterization of their scintillation and imaging properties. The corresponding performance characterization is outlined below.

Decay time measurements: The CsI(Tl) screens can be compared to scintillators currently available for CT scanning, such as for example, GOS(Tb), GOS(Pr), YAG and CaWO$_4$. Decay time measurements involve measurement and study of the decay profiles of the various screens. The screens were excited with 20 ns (FWHM) x-ray pulses with a nominal maximum photon energy of 140 kVp, resembling the energy expected in the current application, using a XRS-3 source (Golden Engineering, Inc.). The scintillation light from the screens was passed through a model 234/302-0.2 m McPherson monochromator, detected by a Hamamatsu R2059 photomultiplier (PMT), and recorded by a Tektronix TDS220 digital storage oscilloscope. Both time and signal domains span nine orders of magnitude. Further, both domains were extended two more orders of magnitude by making additional measurements in which a mechanical shutter simply interrupted the excitation from a continuous x-ray beam (from a Philips source), while the decay of the residual emission was recorded by a photon counting technique.

TABLE III

Properties of powdered screens.

| Material | Column/Particle Size (μm) | Screen Thickness (mg/cm$^2$) | Backing | Lamination/Protective coating |
|---|---|---|---|---|
| CsI Screens | | | | |
| CsI (Tl) | 5 μm diameter | 205 (500 μm thick) | Absorptive | Yes |
| CsI (Tl) | 5 μm diameter | 94 (230 μm thick) | Absorptive | Yes |
| CsI (Tl) | 5 μm diameter | 63 (140 μm thick) | Absorptive | Yes |
| GOS (Pr) | 10-15 | 130 | Reflective | Yes |
| GOS (Tb) Lanex Fast | 10-15 | 130 | Reflective | Yes |
| GOS (Tb) Min R-2000 | 10-15 | 34 | Reflective | Yes |
| YAG | 7-14 | 70 | Reflective | No |
| CaWO$_4$ | 10-15 | 30 | Reflective | Yes |

Figure 3:
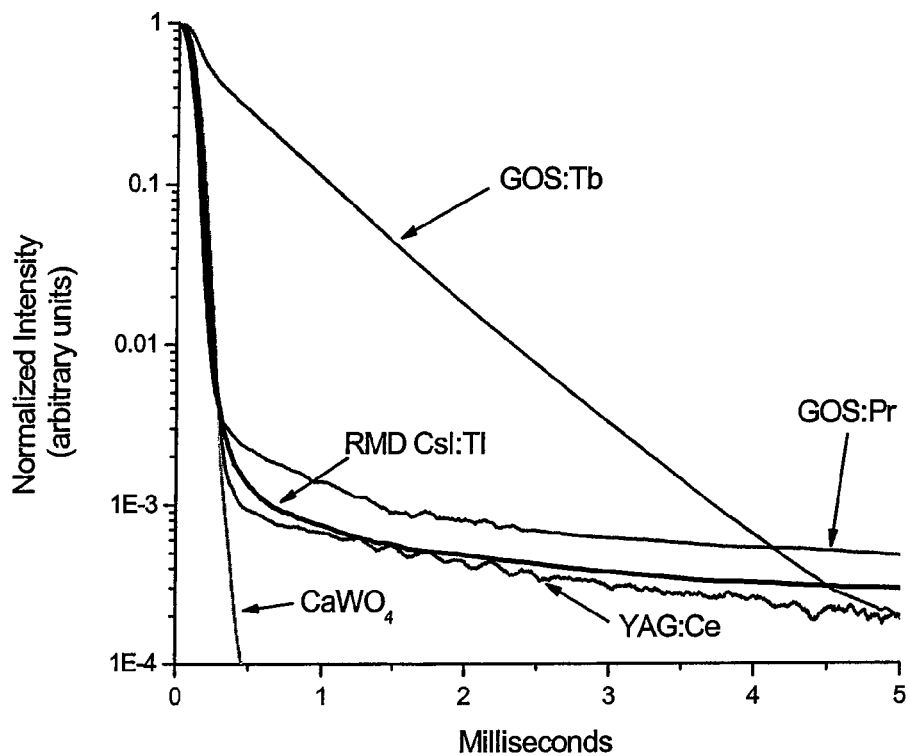
FIG. 3 illustrates decay characteristics of various screens of the present invention, in which all of the screens are fast enough for targeted 300 frame per second (fps) imaging, except GOS(Tb) which may show some image blurring at high frame rates.

FIG. 3 shows decay time characteristics of various screens encompassed by the present invention. As can be seen from FIG. 3, screens made from CsI(Tl), GOS(Pr), YAG, and CaWO$_4$ show a very rapid decay ($\tau=1/e$) of a few microseconds or less, except for GOS(Tb) which decays in approximately 1 ms. Also, most of these screens show finite residual intensity even up to 5 ms after excitation due to their known afterglow characteristics. However, the residual intensity is small enough (<10$^{-3}$ of initial intensity) so that these screens can be used for 300 fps (3.3 ms/frame) imaging. Although GOS(Tb) exhibits a slow decay, it does not have any appreciable afterglow after ms, and it decays to a 0.001% intensity level in 3.5 ms. Thus, all these screens are fast enough for a targeted imaging speed of 300 fps and the ultimate preference depends on the other properties such as their light output efficiency, spatial resolution, noise, and requirements of the specific application.

Spectral analysis: The x-ray excited emission spectra of the scintillator screens were measured using a photomultiplier tube (PMT). Each screen under investigation was excited by the 8 keV x-ray source (Cu K$_\alpha$ line). To generate the required flux at the sample, the x-ray generator was operated at 40 kV with a 20 mAs setting. The resulting scintillation light was collected by the monochromator and the intensity of the selected wavelength was measured using a PMT (RCA model C31034). The operation of the whole instrument including the x-ray trigger, the rotation of the monochromator to select the wavelengths, and the data acquisition and analysis was software-controlled.

Figure 4:
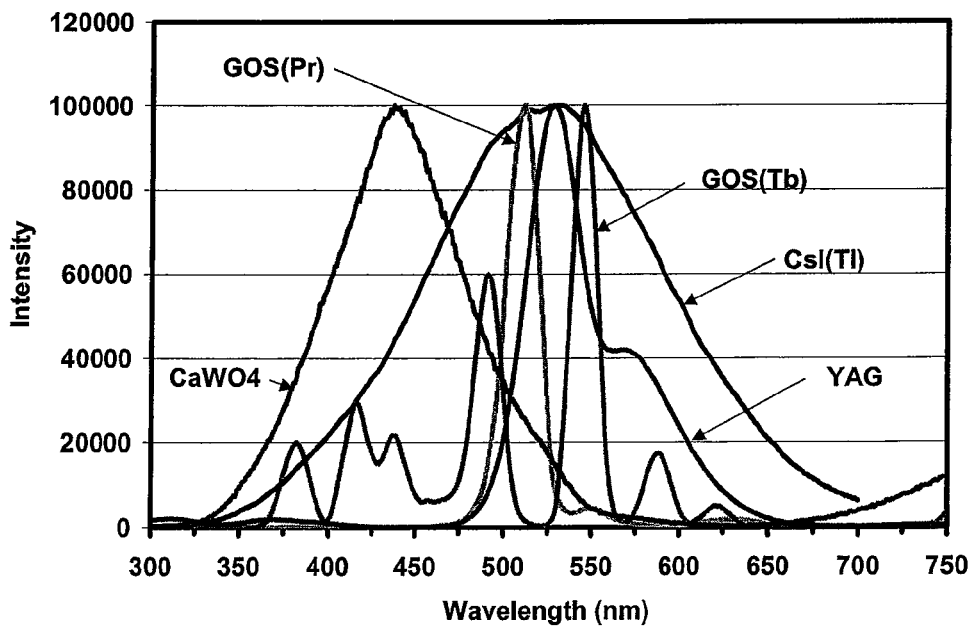
FIG. 4 illustrates spectral emission characteristics of various screens. Except for $CaWO_4$, emission for all the screens peaks in the green region of the visible spectrum, where the front-illuminated IGCCD has a QE (detection efficiency) of 35%.

FIG. 4 shows normalized spectral emission characteristics of various screens embodied by the present invention. Screens of CsI(Tl), GOS(Pr), GOS(Tb), and YAG show peak emission in the 500 to 550 nm range which is well suited for the chosen CCD, showing ~35% of QE in this range. However, the CaWO$_4$ screen shows emission peaks in the 400 to 450 nm range where the CCD QE is only ~5 to 7%. As high speed imaging is inherently light starved, a low CCD QE may not be acceptable due to the resulting low signal-to-noise (SNR), unless a back thinned CCD is used.

X-ray characterization: The light output, signal-to-noise ratios, and spatial resolution performance of the scintillator screens was evaluated by coupling them to a standard CCD system. The CCD system was comprised of a 1K×1K (1024× 1024 pixel) thermoelectrically cooled CCD optically bonded to a 3:1 fiberoptic taper. The CCD pixel size was 19 μm and with the fiberoptic taper the effective pixel size was 57 μm resulting in a Nyquist limiting frequency of 8.6 lp/mm, a performance which was adequate for testing. The CCD device, readout electronics (Including a 12 bit ADC), and the image processing software operated on a PC platform. The x-ray source used for the measurements was a Gendex Series 1000, tungsten target, 40-110 kVp continuously variable energy source. For the measurements reported here, the x-ray generator was set at 40 kVp. The source to detector distance was maintained at 65 cm. During each measurement the exposure was measured using a Nuclear Associates Model 06-526-5280 Rad Check Exposure meter and the data was corrected for any variations in exposure.

Light Output Measurements: Light output measurements were made by exposing the detector to a uniform flood field of x-rays, and averaging the analog to digital unit value (ADUs) in a pre-defined region of interest (ROI). Calculation showed that 400 μm thick CsI(Tl) should stop about 97% of 40 keV x-ray, whereas a 150 μm thick CsI(Tl) film should attenuate about 81%. For each measurement the x-ray exposure was estimated using an air ionization chamber (about 4 mR). Several measurements per screen were made to improve the statistical accuracy of the ADU value. These data were corrected for any variations in the measured x-ray exposure. The signal-to-noise ratio (SNR) in each screen was computed by dividing the average ADU value by the measured standard deviation in the flood image.

Figure 5:
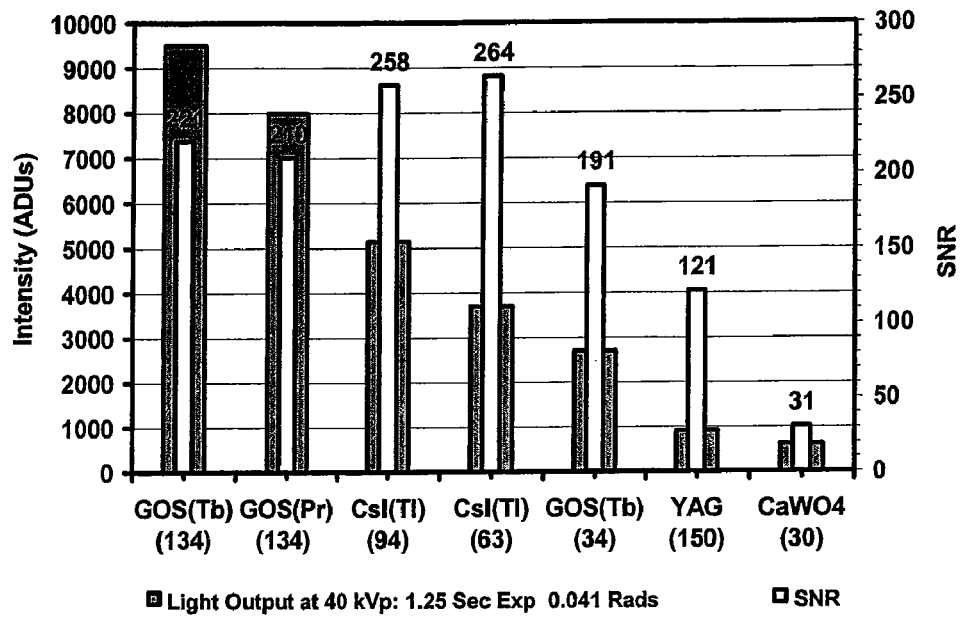
FIG. 5 illustrates the light output of various screens under identical x-ray exposure. The corresponding signal-to-noise ratio (SNR) is also plotted.
Figure 6:
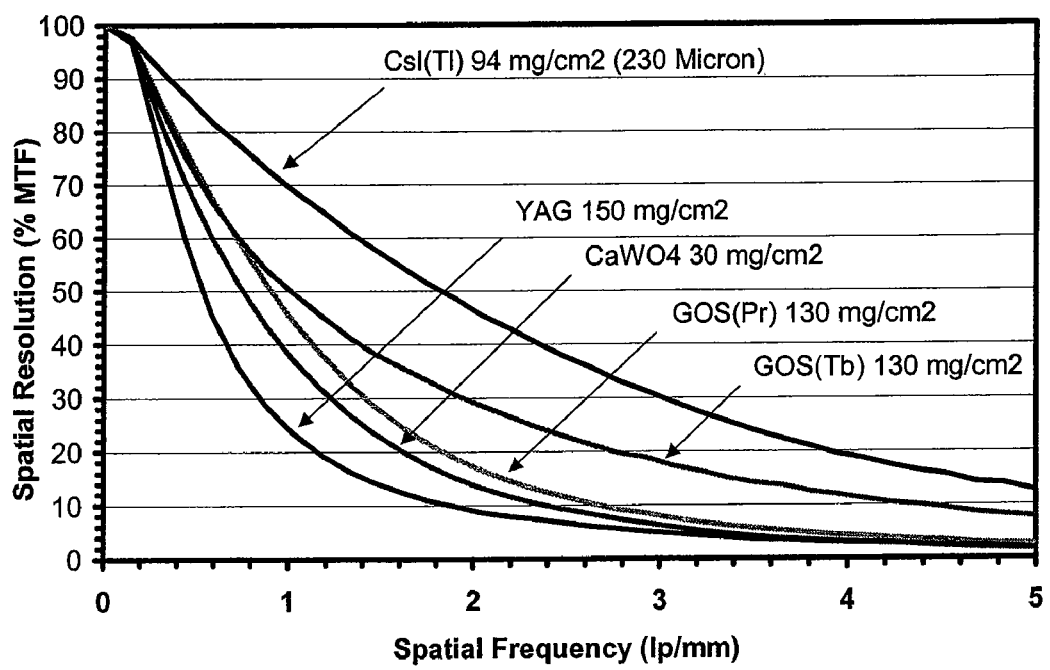
FIG. 6 illustrates spatial resolution of various screens.

FIG. 5 and FIG. 6 depict the comparison of light output of various screens measured at 40 kVp and 0.04 Rads of exposure as well as measured SNR. Here, the intensity was plotted on the Y axis in the Analog to Digital Units (ADUs), and the screen ID were plotted on the X axis. Numbers in parenthesis next to the screen ID represent its mass thickness in mg/cm$^2$.

As can be seen from FIG. 5, GOS(Tb) produces the highest light, but has lower SNR due to its known noise properties. The GOS(Pr) is brighter, relatively faster (2700 ns), and has no afterglow. As such, the screen comprising GOS(Pr) can be used for the disclosed application. The CsI(Tl) screen exhibited excellent light output, even though it was significantly thinner than GOS(Tb) and was deposited on an absorptive backing. This was attributed primarily to the high scintillation light yield of CsI(Tl) (60,000 ph/MeV), which significantly improves SNR. Our prior experience shows that the presence of a reflective backing can further enhance CsI(Tl) light output by at least a 30%. Thus, due to its excellent light output, fast decay (~1 µs, FIG. 3), relatively low afterglow, and excellent spatial resolution arising from its microcolumnar structure, the CsI(Tl) is a preferred embodiment for high quality imaging with imaging speeds to 500 fps and higher.

Among the YAG and CaWO$_4$ screens, YAG showed higher light output than the CaWO$_4$, however the total light output was substantially lower than CsI(Tl) or other screens. It should be noted that both YAG, and CaWO$_4$ intrinsically have a good light output and a high x-ray to light conversion efficiency. As such, screens fabricated using these materials are expected to show much higher light yield than what was measured. The poor performance of the YAG screen may be due to very high thickness of the screen (150 mg/cm$^2$), which causes self-absorption.

In a separate analysis a 400 µm (180 mg/cm$^2$) and 150 µm (67 mg/cm$^2$) CsI(Tl) screens were examined. The 400 µm CsI(Tl) screens produced about a 3600 ADU signal. This was consistent with the expected x-ray absorption in respective screens. Also, as can be seen from FIG. 6, the CsI(Tl) screen exhibited excellent light output and higher SNR than the commercial GOS phosphor. This was attributed primarily to the higher scintillation yield of the CsI(Tl) (60,000 photons/MeV), higher x-ray attenuation, and excellent response uniformity across the screen area. The presence of a reflective backing can further enhance CsI(Tl) light output by at least 30%.

Figure 7:
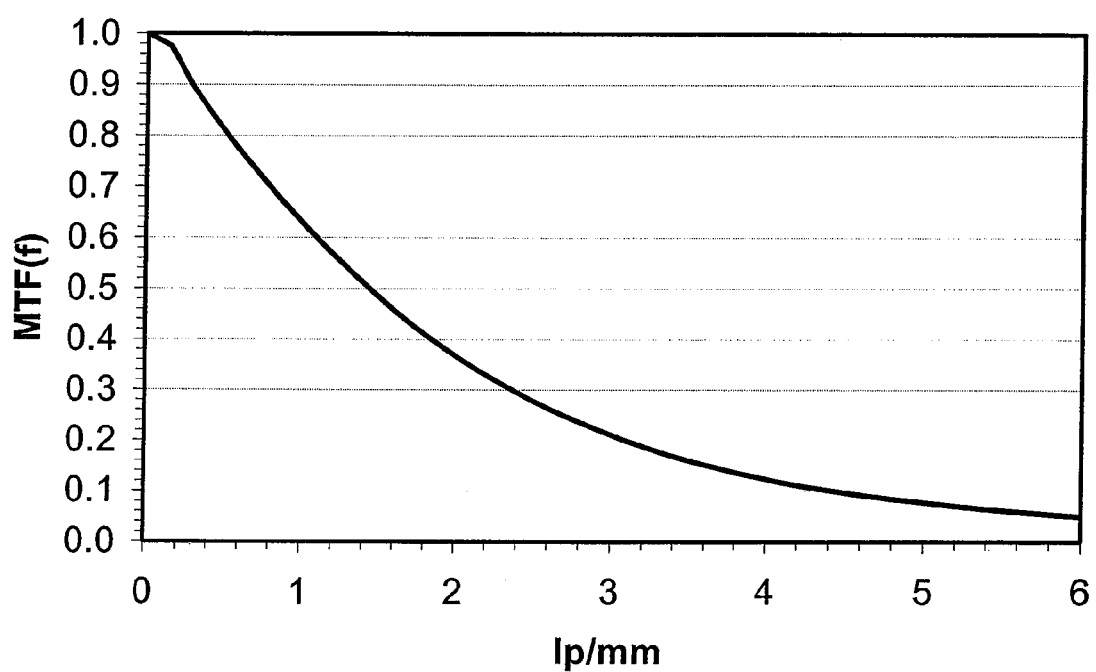
FIG. 7 depicts the spatial resolution of a 400 μm thick CsI(Tl) screen showing limiting MTF(f) of 5 lp/mm.

Spatial Resolution Measurements: To evaluate spatial resolution of the screens, the pre-sampling spatial resolution, modulation transfer function (MTF) was measured according to the technique described by Fujita et al., (*IEEE Trans. Med. Imaging MI* 11:34-39 (1992)) and others. In such techniques, an image is obtained of a long, 10-µm (±1 µm) wide slit made of 1.5 mm thick tantalum that is placed at a slight angle (less than 4 degrees) to the pixel matrix at the center of the detector. The area around the slit was covered with 0.5 cm thick lead. The slit was placed in contact with the surface of the imager so that the spreading of the Line Spread Function (LSF) due to the finite size of the focal spot did not pose a significant limitation. The exposure was adjusted by varying the mA of the output while maintaining a constant 40 kVp, to ensure that the tails of the LSF had no significant electronic noise. The finely sampled LSF was normalized to a peak value of one. The Fourier Transform (FT) of the finely sampled LSF was performed to provide the pre-sampling MTF. FIG. 6 depicts the measured MTF as a function of spatial frequency for thick screens. FIG. 7 shows the measured MTF as a function of spatial frequency for a 400 µm thick CsI(Tl) screen. As is known in the art, "thick" and "thin" screens are relative to spatial resolution or pixel size, and will vary depending on the desired spatial resolution.

CsI(Tl) screens show substantially higher MTF compared to the other screens of comparable thickness. Specifically, the 230 µm thick screen (94 mg/cm$^2$) demonstrated a resolution of >5 lp/mm. While not shown in FIG. 6, a 140 µm thick screen showed a resolution of >10 lp/mm. When combined with its high light output, low noise, and excellent speed of response, CsI(Tl) appeared to be the best choice for the detectors of the present invention. Also, thick GOS(Pr) (130 mg/cm$^2$) demonstrated respectable 2.5 lp/mm resolution. Although the resolution is not as high as the CsI(Tl), with its high light output, rapid decay, and absence of substantial afterglow, GOS(Pr) screens may also be a good choice for some applications.

As expected, thinner screens showed higher MTF compared with thicker screens. The 150 µm CsI(Tl) screen (67 mg/cm$^2$), which is twice as thick as GOS, demonstrated comparable resolution to the GOS screen (34 mg/cm$^2$ screen; FIG. 6). Also, the 400 µm thick screen demonstrated well over 3 lp/mm of resolution or the resolution of about 160 µm. It should be noted that the MTF(f) demonstrated here was lower than the actual MTF(f) due to the presence of a 3:1 fiberoptic taper with known distortions and light spreading effects. When coupled to a defect free taper even better screen performance is expected.

Detective Quantum Efficiency (DQE(f)) measurements: The detective quantum efficiency measurements were performed for two screens, a 140 µm thick CsI(Tl) film and a Kodak Min-R 2000 screen. Thus, the data provides a direct comparison between the performances of two competing technologies, a GOS screen and a CsI(Tl) screen. Data were acquired by coupling each of the screens to a Dalsa-Medoptics CCD, which comprises of a 1K×1K pixel Kodak® KAF-1000 sensor optically bonded to a 2:1 fiberoptic taper. With the presence of a fiberoptic taper, the effective CCD pixel size is 48×48 µm$^2$ and an effective active area is ~5×5 cm$^2$. The x-ray generator used for these measurements was a Source-Ray Inc. SB-80-500-DI tungsten anode generator operated at 40 kVp with 0.5 mm of added Al filtration. The source-to-imager distance was maintained at 120 mm. The exposure measurements were made using a Keithley/Inovision 35050A dosimeter equipped with a model 96035B ion chamber (Inovision, Cleveland, Ohio). In order to calculate the value of the photon fluence, the x-ray spectrum was measured using a 3×3×2 mm$^3$ single pixel cadmium-zinc-telluride (CZT) detector (Amptek, Inc. Bedford, Mass.). This spectrum, along with the standard table of dose/photon as a function of energy, was used to estimate average exposure in mR/photon. The measured exposure was divided by the average mR/photon value to calculate photons/mm$^2$/mR. A detailed description of the specifics of measurement of the incident x-ray spectrum has been published. (Vedantham et al., *Med. Phys.* 27:558-567 (2000); Vedantham et al., *Med. Phys.* 27:1832-1840 (2000)).

The DQE(f) of the imaging system was calculated from the measured presampling MTF, the NPS$_{normalized}$(f) (Noise Power Spectrum, the frequency-dependent noise) and the signal-to-noise ratio (SNR) of the incident x-ray spectrum. The DQE(f) of the imaging system is calculated as:

$$DQE(f) = MTF^2(f)/(SNR^2 \cdot NPS_{normalized}(f))$$

$$DQE(f) = \frac{MTF^2(f)}{SNR^2_{incident} \cdot NPS_{normalized}(f)}$$

Figure 8A:
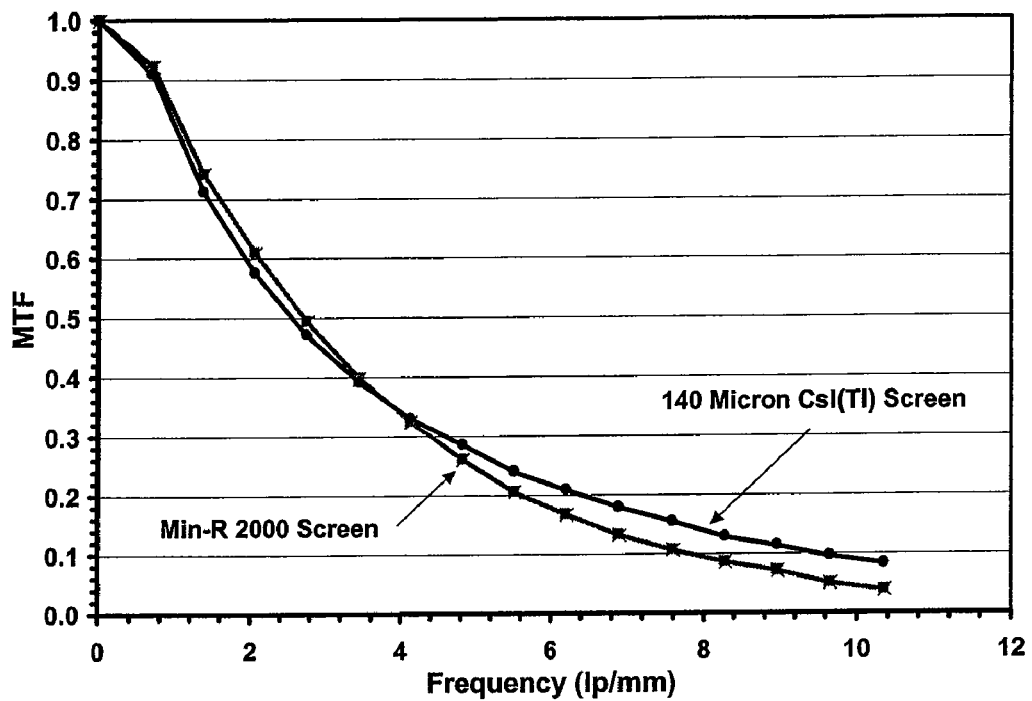
FIG. 8(a) Spatial resolution (MTF, modulation transfer function) 8(b) NPS, noise power spectrum) and 8(c) DQE of the 140 μm thick CsI(Tl) screen and the Min-R 2000 GOS (Tb) screen, measured under an identical x-ray exposure of 12.5 mR.
Figure 8B:
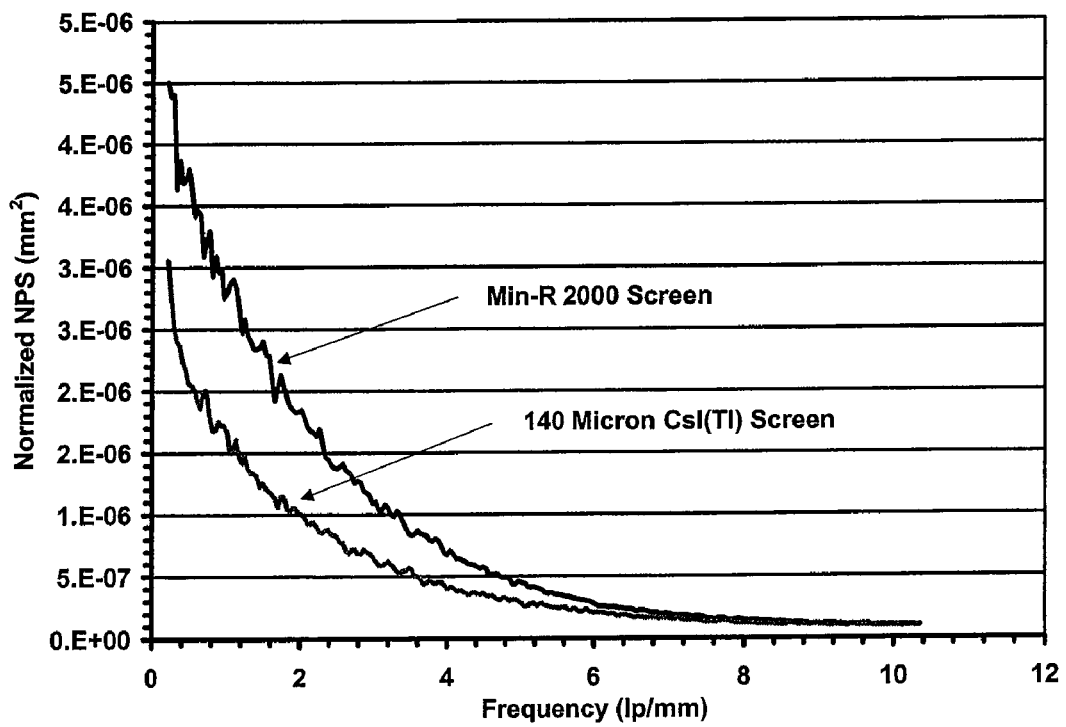
Figure 8C:
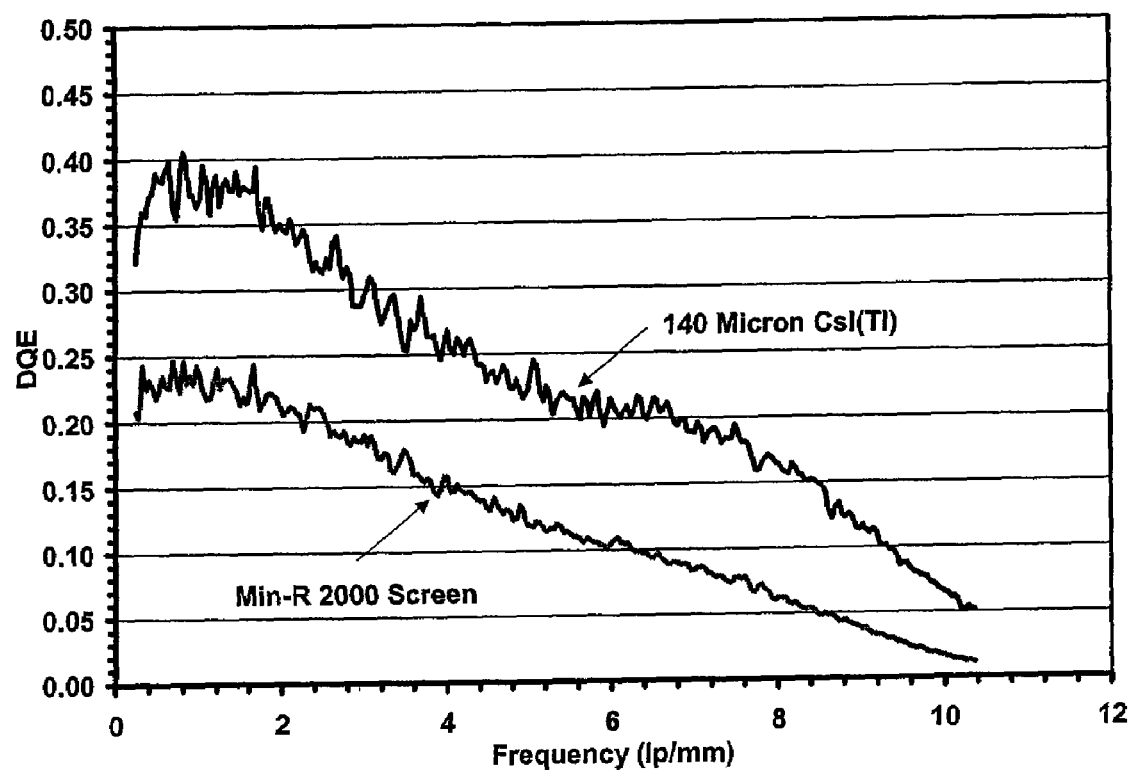

FIGS. 8(a) to 8(c) shows the MTF, NPS and resultant DQE using the screens under evaluation for a 12.5 mR exposure. The data show significantly higher DQE(f) using CsI(Tl) screens. As the DQE performance of an imaging system represents the signal-to-noise ratio (SNR) transfer characteristic and the dose efficiency of the system, improved DQE performance would imply the ability to provide equivalent image quality at a lower dose. Alternately, improvement in DQE performance would indicate that superior image quality could be obtained if a constant dose level is to be maintained. Although the data demonstrate improved performance from CsI(Tl) over a wide frequency range, the response is particularly accentuated in the lower line pair region. Improved DQE performance at low spatial frequencies would indicate the ability to provide images with improved contrast.

Based on the data presented here, it was demonstrated that the microcolumnar CsI(Tl) scintillator is a preferred embodiment for high speed imaging, although different screens may be suitable for different applications and speed with which data are acquired. For example, $Gd_2O_2S(Pr)$ screens with 130 mg/cm$^2$ thickness may be used for high energy (120 to 140 kVp) applications where a premium is placed on light output only, not on SNR and spatial resolution. An advantage of such a screen is that it is cheaper to produce than CsI.

Light Coupling Scheme

A CCD based x-ray imaging detector can either be lens coupled or fiberoptic coupled to the scintillator. The choice of coupling is based on performance and cost requirements. While costly, fiberoptic coupling is generally preferred for improved light coupling efficiency. The cost depends on the size and shape of the required fiberoptic. In one test embodiment, the CCD dimensions are 0.82×0.82 cm$^2$ and the active area required to image a small animal is about 7×7 cm$^2$. Thus, a fiberoptic taper with 8.5:1 reduction ratio is needed, which is currently impractical, since tapers with a maximum of 5:1 reduction ratio can be practically fabricated. Beyond this, the cladding at the small end of the taper becomes too thin for a fiber to act as a light guide, and also a significant amount of distortions are introduced, typically greater than about a 75 to 100 microns line shear. Such distortions produce light cross-coupling in fibers and distortions in the image, resulting in reduced resolution and loss of signal to noise ratio. Furthermore, the numerical aperture at the large end of the taper becomes too narrow to efficiently couple the light. Finally, the cost of such a component is substantially high due to the difficulties in its manufacturing process. Thus, to provide the approximately 7×7 cm$^2$ coverage that would be suitable for scanning a small animal using a 0.82×0.82 cm$^2$ CCD, a lens coupling is a better choice with current technology in spite of its low efficiency. Nevertheless, nothing in the present invention precludes the use of fiberoptic coupling as the technology for their production improves. A lens coupling as typically used in microCT devices is well known to the skilled artisan and is appropriate for use in the present invention. A brief description of the requirements of a lens coupling for the present system is provided below.

Several authors have addressed the subject of light coupling efficiency of lens based x-ray imaging systems (Tong and Boon, *Med. Phys.* 24:565-570 (1997); Maidment and Yaffe, *Phys. Med. Biol.* 41:475-493 (1996); Hong et al., *Med. Phys.* 21:1193-1197 (1994)). Assuming the scintillator screen to be an extended Lambertian source, the light coupling efficiency of the lens is given by:

$$g = T/(4(F\#)^2(1+M)^2+1) \quad g = \frac{T}{4(F\#)^2(1+M)^2+1}$$

Where F# is the F-number of the lens, M is the demagnification ratio (Object/Image), and T is the bulk transmittance of the lens. For the system tested, the lens F# is 0.95, M=8.5, and T=80%, which results in an efficiency of 0.25%. Although this efficiency is low, the 10×10 cm$^2$ CsI(Tl) screen based system with the estimated efficiency of only 0.12% produces enough light to generate a good quality image using a mini focused x-ray source.

Figure 9:
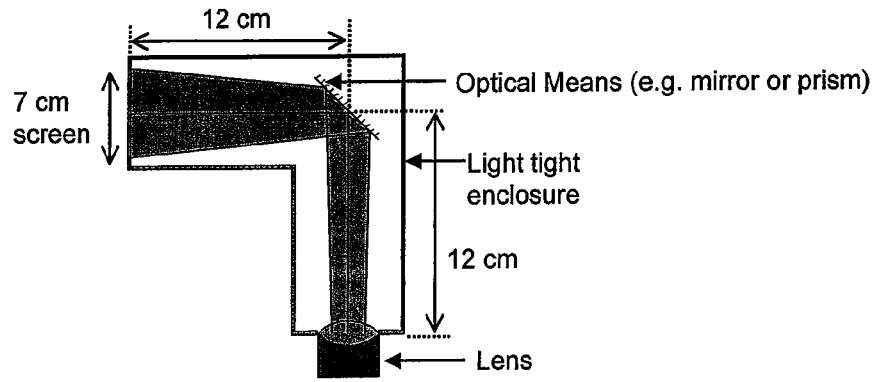
FIG. 9 is a schematic of the detector housing.

Detector housing: Placing the detector directly in line with the x-ray source resulted in the presence of spurious light flashes (e.g., saturated pixels) scattered randomly in many of the images. These bright spots were attributed to direct x-ray hits in the CCD and result in line artifacts in the reconstructed data. To avoid these phenomena, the detector can be housed in an L shaped enclosure as shown in FIG. 9. Software methods can also be used to ameliorate this effect. One such method searches for very high intensity pixels that have no neighbors of similar intensity, and replaces the targeted pixel's intensity value by an average intensity value calculated from the intensity value of its neighbors.

In such an embodiment, the scintillator screen can be imaged by the camera using a first surface of a high quality mirror or a prism. Adequate shielding can be added to the detector end to minimize scatter in the CCD housing. The front end of the detector housing can have a Be window for a maximum x-ray transmission. Also, the entire housing can be made light tight to reduce the ambient light.

Light Detector

Internal Gain CCD Detector

This invention takes advantage of a new internal gain CCD camera which has become available. This camera is based on a E2V internal gain CCD (Roper Scientific, Trenton, N.J.). Table IV lists the performance specifications of this CCD. Of course, the invention need not be practiced with just this particular internal gain CCD (IGCCD). For instance, the Cascade 512F camera developed by Roper Scientific, NJ has also been used. As demonstrated, this is an excellent choice for high speed x-ray imaging. The system uses a front illuminate internal gain CCD chip (E2V CCD87). This CCD has a 30% quantum efficiency at the 540 nm light produced by CsI(Tl) and other fast phosphors tested. A new, back thinned version of the same CCD is now available and shows approximately 95% QE at 540 nm. This is particularly important for low light imaging where SNR mainly depends on the input shot noise. It is estimated that a factor of 3 gain in QE for the present application would improve the SNR approximately by a factor of 2, making a substantial difference in the image quality for a given x-ray exposure. Alternately, this will allow data capture at higher speeds to minimize x-ray exposure to the animal.

The new internal gain CCD, developed by Marconi (now marketed by E2V Technologies), works like a conventional CCD, except that it provides an internal gain via an avalanche mechanism. This new device combines properties of two well-known silicon detector properties, the high resolution and low noise of a CCD, and the internal gain and very high sensitivity of an APD. Thus, an imaging system based on the IGCCD does not require the use of intensification stages even though it provides detection of extremely low light levels. In contrast to the intensified CCDs (ICCDs), the IGCCD provides superior quantum efficiency over 400 nm to 1050 nm wavelengths, substantially better resolution (MTF(f)), significantly wider dynamic range, and low sensitivity to over-exposures, resulting in an improved image quality at a lower cost.

Figure 10:
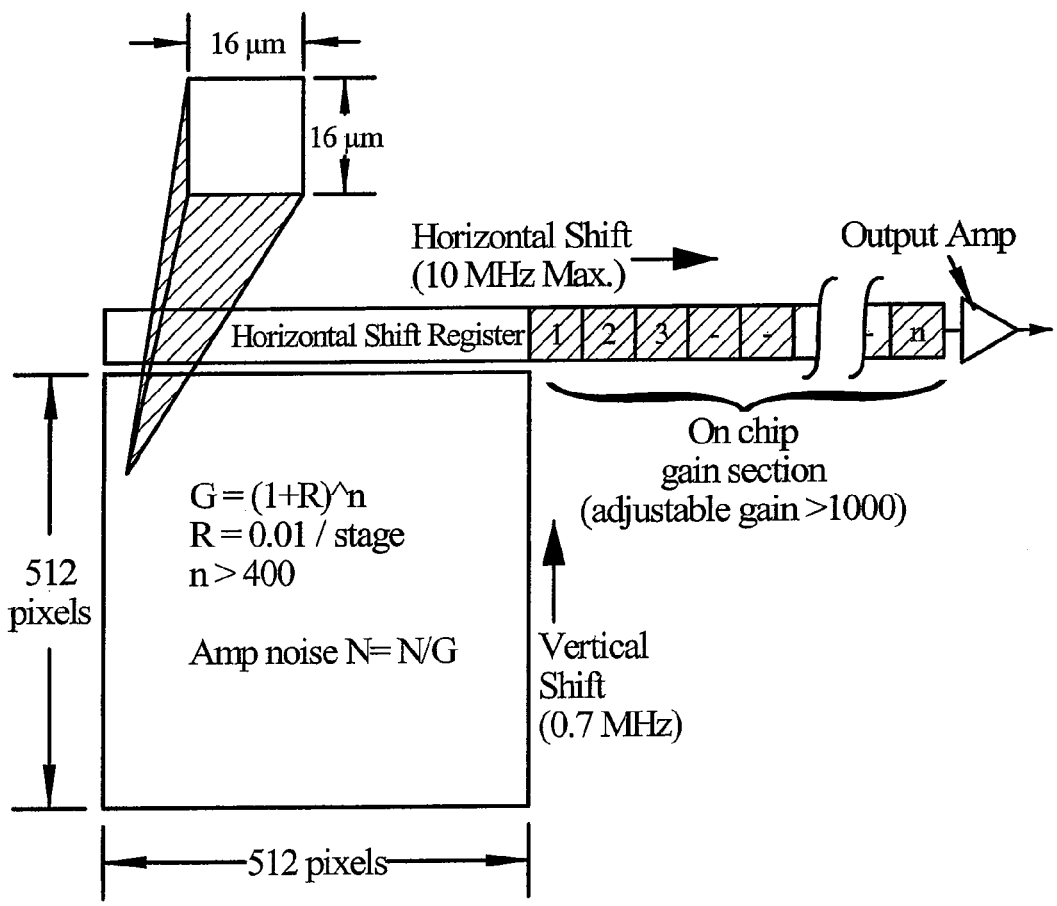
FIG. 10 is a schematic of the IGCCD architecture.

FIG. 10 depicts a schematic of an IGCCD encompassed by the present invention. The device, model # CCD87 manufactured by Marconi E2V Technologies, is a frame transfer device which operates in inverted mode to suppress dark current (Table IV). It comprises of a 256 K pixel image zone formed by 512×512 pixels, each measuring 16×16 µm in size. An additional 512×512 pixel area, which is masked by an optical shield, is used as an on-chip frame storage zone. During conventional operation, the imager integrates the image for a specified time, and then the image is shifted rapidly out of the image zone and into the shielded frame storage zone. The vertical shift rate during this transfer is 1.6 µs per row and there are 512 rows of image data. Therefore, a single image is transferred in the on-chip memory zone in 820 µs. This fast data transfer into the storage zone allows the IGCCD to perform imaging at high speed. Specifically, when used with a continuous (CW) x-ray source the image transfer can occur without significant blurring, eliminating the need for an x-ray shutter (which slows down the imaging process).

TABLE IV

IGCCD Camera Specifications

| Parameter | Specification |
|---|---|
| CCD Chip | E2V CCD87 |
| CCD Format | 512 × 512 Pixels |
| Pixel Size | 16 µm Square |
| Full well capacity | 250 ke$^-$ |
| Gain register capacity | 850 Ke$^-$ |
| Readout | 16 bits; 10 MHz |
| On-chip gain | 1 to >1000x |
| Operating temperature | −30 ° C. |
| Dark current | 1 e$^-$/pixel/sec @ −3° C. |
| Binning | Flexible binning |

After the image is transferred into the frame storage zone, the data is shifted up vertically one row at a time into the serial register. Once in the serial register, charge packets are individually shifted toward the output amplifier and the operation is repeated until the entire image is read. In our existing system, the serial readout was performed at a rate of 10 million pixels per second, thus the entire 512×512 pixel data was read out in ~26 ms or a maximum speed of ~30 frames per second with additional overheads. Higher frame rates of 300 fps and above can be achieved by sacrificing the pixel resolution as shown in Table V.

TABLE V

Measured frame rate for the Cascade 512F camera with full pixel resolution. Higher framer rates can be achieved by pixel binning.

| Pixel Resolution | Measured Frame Rate (Frames/second) |
|---|---|
| 512 × 512 | 30 |
| 512 × 256 | 60 |
| 512 × 128 | 120 |
| 512 × 64 | 240 |
| 512 × 32 | 480 |

This feature has been used to image 512×128 pixels at the frame rate of ~120 fps. Note that this speed can be further increased by implementing high pixel readout rates of 20 MHz.

To facilitate internal gain, the serial register of the IGCCD is extended by additional "n" stages", which are collectively termed as an "on-chip gain section". Charge transfer into the gain section of the CCD structure results in avalanche multiplication. The amplitude of the clocking signal applied to the serial shift register controls the gain (R) of each of the stages. With "n" gain stages, the overall gain, G, becomes:

$$G=(1+R)^n$$

Typically, n is greater than 400, resulting in a typical gain of 50. This gain can be varied from 1 to 1000 by selecting the amplitude of the clocking signal. An important advantage of the gain is that the "effective read noise" N of the on-chip amplifier is reduced by the gain factor since effective nois=N/G. Thus, the internal gain and reduced amplifier noise result in a significantly improved SNR. This is particularly relevant for high-speed imaging where signal strength is low. To minimize the loss of dynamic range due to internal gain, the well capacity of the pixels in the gain register is substantially enhanced (850 Ke$^-$ as oppose to 250 Ke$^-$). This allows the use of maximum gain without the loss of effective dynamic range of the CCD.

Figure 11:
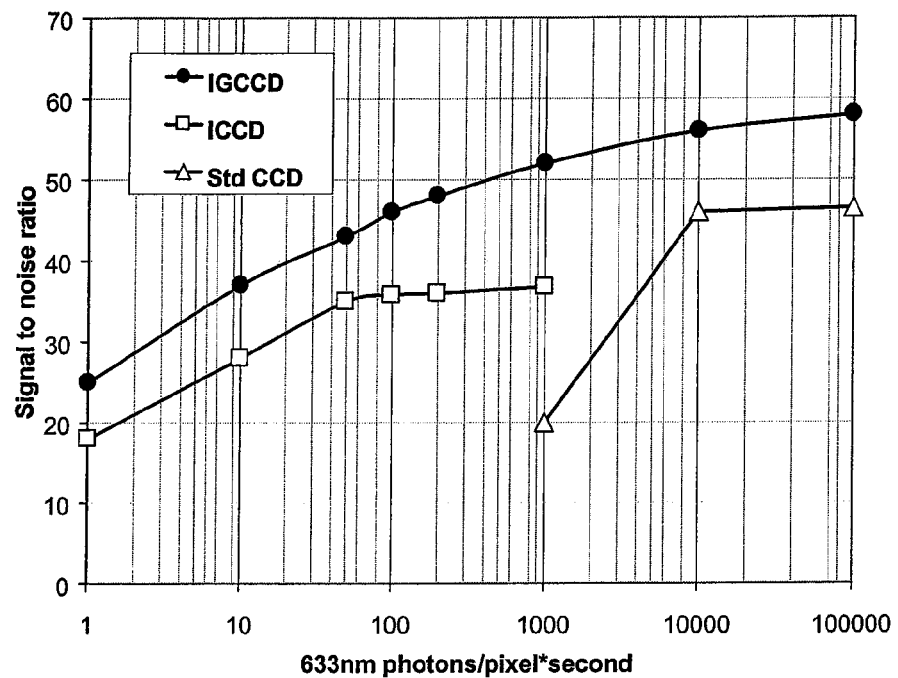
FIG. 11 illustrates SNR vs. Illumination for the front-illuminated IGCCD, a standard commercial CCD and an intensified CCD using Omni 4 advanced image intensifier.

FIG. 11 shows the measured SNR for an IGCCD, a standard commercial CCD and an intensified CCD using an Omni 4 advanced image intensifier. As can be seen from FIG. 12, using the IGCCD a single 633 nm (red) photon can be detected with a SNR of 25. The large full well capacity of the IGCCD, typically 250,000 e$^-$, when combined with the higher SNR results in a much wider dynamic range than is possible with either the intensified CCD or a conventional CCD.

IGCCD Camera Characterization

To maintain the high SNR in high speed imaging, the total system noise should be as small as possible and the sensitivity should be high enough to efficiently detect the passive light from the scintillator screen without degrading the overall dynamic range.

Dark noise: The dark signal of a CCD array refers to the thermally generated electrons in a pixel even in the absence of incident signal photons. The rms variation in the dark signal is the dark noise of the device. For the current IGCCD camera, the measured dark noise is rated at 1 e$^-$/pixel/second at −30° C. When operated at high frame rates, this noise is <<1e$^-$, and is insignificant. A moderately cooled CCD may be used (to save cost), which is expected to raise this noise floor to ~20 e$^-$/pixel/second at 0° C. When operated at 30 fps or higher this will still result in a negligible dark noise.

Figure 12:
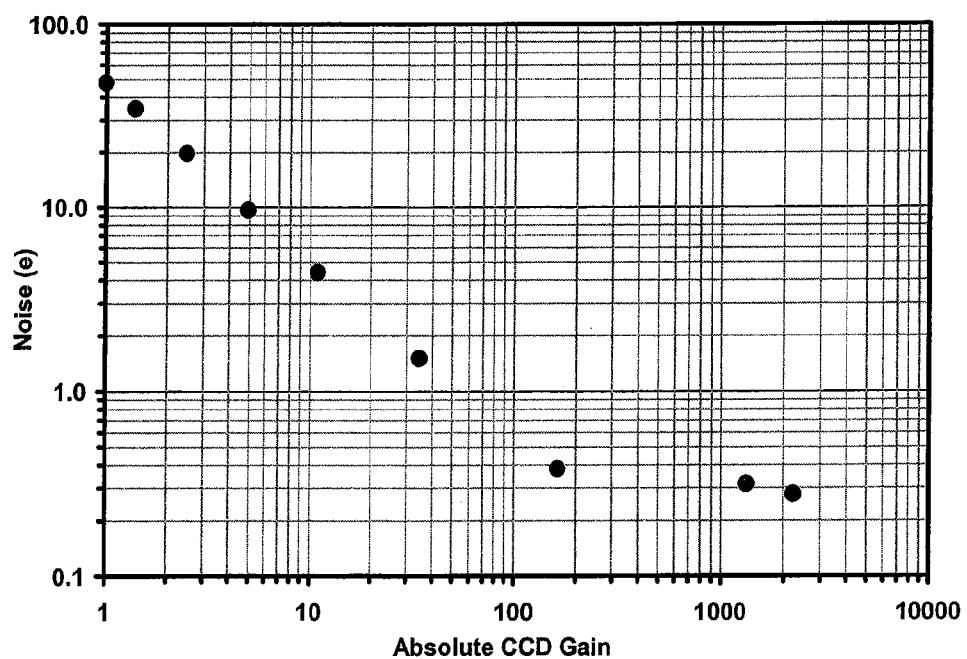
FIG. 12 illustrates effective system read noise as a function of gain setting (in ADUs). For gains >50, the effective read noise is <1e$^-$.

Effective read noise: To measure the read noise, the system was operated at the maximum speed of 10 MHz and at various internal gain settings. For each gain setting, two consecutive dark images were acquired and digitally subtracted. The value of the standard deviation in the subtracted image represents the read noise. The process was repeated several times to improve statistical accuracy of the measurement. The resulting read noise was divided by the gain to obtain the effective read noise. FIG. 12 depicts the effective read noise as a function of the internal gain setting (ADUs), which shows that for the gain of ~50 or more, the noise is <1e$^-$. Thus, even for high readout speeds, the effective read noise is quite low or negligible, such as for example, below 1 electron at gains of about 50.

Internal gain: The amount of gain applied in the output stage of the IGCCD is adjustable through serial port camera command issued by the user (by externally adjusting clock amplitudes in the gain register). The Roper camera allows gain settings of 0 to 4095 ADUs (corresponding to the absolute gain of 1 to over 3000).

Unlike image intensifiers where gains may be thousands or tens of thousands, the IGCCD needs only enough gain to overcome the on-chip output amplifier noise. High gains may be used for low light detection at the cost of reduced dynamic range as discussed below. Thus, the ideal level to operate the camera is at absolute gain of ~50 or the DAC setting of 3500 ADUs if the camera speed was set at 10 MHz.

Dynamic range: While the presence of internal gain boosts the system SNR, it also reduces the effective dynamic range of the system. As an example, for the E2V CCD 87 (the IGCCD chip), the loss of dynamic range is partly compensated by increasing the full well capacity of the readout register where avalanche gain occurs. Specifically, the full well capacity of the image pixel in the CCD is 250 Ke$^-$ and that of the gain register pixel is 850 Ke$^-$. Thus, if the device is operated at a gain of 50, the maximum usable pixel well capacity is 850,000/50 or 17,000 electrons, or 14 bits. Since the dark and read noise is negligible, most of this dynamic range is useful. The loss of dynamic range with the internal gain setting is given in Table VI.

TABLE VI

Relationship between the internal gain and effective dynamic range

| Internal Gain | Effective Pixel Well Capacity (e$^-$) | Dynamic Range (Bits) |
|---|---|---|
| 50 | 17,000 | 14 |
| 100 | 8,500 | 13 |
| 200 | 4,250 | 12 |
| 500 | 1,700 | 11 |
| 1000 | 850 | 10 |

Sensitivity: To measure the sensitivity, the IGCCD camera was mounted on an optical bench and a laser beam was used to illuminate pixels. The camera lens was removed, and a 540 nm (green) collimated laser beam was made incident on the IGCCD chip. The camera was operated at 10 fps, and at full gain (maximum DAC setting of 4095). The photon flux was measured with two independent systems, a Hamamatsu calibrated photodiode (1336-8BQ) and a ThorLab power meter (S20mM). Metallic neutral density filters (ThorLabs) were added in the path of the laser beam to attenuate the incident flux until the image could be barely seen on the monitor. The measured fluence for this setting was 4 photons/pixel, indicating that camera was sensitive to 4 green photons.

The significance of this result is that the described detector based on IGCCD is able to detect extremely low levels of light, even though the QE of the CCD for 540 nm light is only 30%. It should be noted that conventional front illuminated CCDs cannot register a signal below ~30 optical photons. Thus, with its internal gain and low read noise, the disclosed IGCCD can provide very low detection levels. If necessary, further sensitivity may be achieved through the use of a back thinned device that offers 95% QE at 540 nm light.

High speed x-ray imaging: For ascertaining the dynamic x-ray imaging capability of the system, a mechanical, steel toy comprising several wheels was used as a test object. The toy could be "wound up" and on release, the various wheels would move at varying speeds of 60 to 120 rpm, providing a dynamically moving test object. This toy (FIG. 13(a)) was exposed to an Electromed x-ray source set at 120 kVp and 50 mA running in continuous mode. The X-ray images of the toy were obtained with various scintillators lens-coupled to a Cascade 512F camera via a mirror positioned at 45 degrees to the optical path. The total working distance was about 25 cm and the camera gain was set at ~40 in these experiments. Dynamic x-ray images of the moving parts of the toy acquired with a 230 μm thick CsI(Tl) screen at speeds of 30, 50, 90, 120 and 225 fps and are shown in FIGS. 13 (b) to 13(f), respectively. As pointed out previously, with increasing frame-rates (speeds), the effective imaging area of the camera is reduced in the vertical dimension, in order to accommodate the faster read-out times. The movement of various wheels in the toy was seen much more clearly when successive images were observed in the "cine" mode (dynamic replay) as compared to the static images shown here.

As can be seen from FIGS. 13(a) to 13(f), at low speeds of 30 fps, the higher speed motion of the gears reduces spatial resolution. As the imaging speed was increased, the motion of the gears was "frozen", thus significantly improving the resolution. It was estimated that the x-ray flux at 224 fps speed was about 0.22 mA per frame, which proved sufficient for the detector.

Contrast agent imaging: In order to establish feasibility of the system for use in perfusion studies, dynamic imaging experiments were conducted with a contrast agent moving through a thin capillary. A low-power submersible pump (Edmund Scientific model 30603-07) was attached to a thin (800 μm inner diameter) Drummond disposable pipet to propel an iodine-based contrast agent (BTF, 0.2% titratable iodine) through the pipet at a speed of approximately 4 cm/s. The Ecomed x-ray source was operated at 70 kV and 100 mA in a constant mode. The camera was operated at a multiplication gain of 50. FIG. 14(a) to FIG. 14(d) demonstrate the unprocessed dynamic x-ray images acquired with a CsI(Tl) screen lens-coupled to the Cascade 512F camera via a mirror as described above, at frame rates of 30, 50, 90 and 120 fps. The leading edge of the iodine bolus was approximately at the middle of the capillary length in each image. The movement of the iodine in the capillary was of course seen much more clearly when successive images were observed in the "cine" mode (dynamic replay) as compared to the static images shown here.

In cine mode images, the resolution was sufficient to observe air bubbles formed in iodine (~400 μm in diameter). Image processing such as flatfield correction and logarithmic transforms is expected to further improve the image quality significantly. These data show the potential of this detector to obtain high speed, x-ray images of good quality in volumetric dynamic studies in small animals, and demonstrate the feasibility of the disclosed detector approach.

Figure 15B:
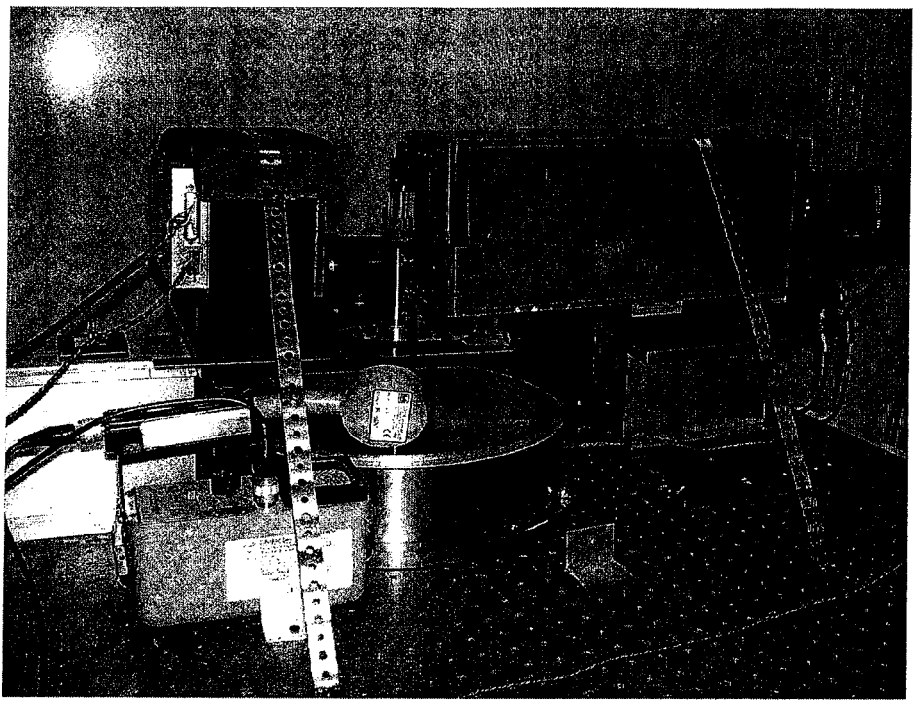

Integrated demonstration: To demonstrate the feasibility of high speed CT imaging, a detector was incorporated into the existing microCT setup (ImTek, Inc., Knoxville, Tenn.). Cone beam CT data on a mouse phantom were acquired at various frame rates ranging from 30 fps to 120 fps using a 230 μm thick CsI(Tl) scintillator screen, a GOS(Pr) screen, and a standard Kodak® Min-R2000 GOS(Tb) screen. In each case, the entire 360° projection data set was acquired in 12.4 seconds, corresponding to the fastest allowed speed of the rotation stage. FIG. 15(a) and FIG. 15(b) illustrate the integrated setup.

In the integrated setup of FIG. 15(a) and FIG. 15(b), the detector comprises the lens based IGCCD camera attached to a specially designed light tight box. The front end of the light tight box was covered with a low x-ray absorption Be window. A sliding assembly was incorporated in the box to mount 10×10 cm area scintillator and to adjust its position relative to the CCD. A 0.95 f# fast lens was used to directly image the scintillator screen onto the CCD chip (without a mirror). To ensure high sensitivity and low noise, the CCD gain was set at 50 which provided maximum dynamic range of 14 bits. The source to detector distance was 12.2 cm and the source to object distance was 9.5 cm. This resulted in the image magnification of 1.28.

A digitally controlled stage (object positioning unit or OPU) was used to rotate the test phantom to obtain 360° projection data. This stage offered a maximum speed of 29°/second or ~12.4 seconds for a full rotation. To ensure coverage of 360°, data were acquired for 15 seconds. For example, at 120 fps, the total number of images acquired were 120×15=1800. A potential disadvantage of this scheme is that a slight misalignment between the 1$^{st}$ image and the image corresponding to the full 360° rotation may occur. However, it was determined that this would have a negligible impact on the reconstructed data due to sub-degree sampling (4 images/° at 120 fps and 1 image/° at 30 fps).

The x-ray source used was a SRI, Inc. Model SB-80-500, 40 Watt, tungsten anode x-ray generator with a 50 μm focal spot. The output range on this source is 30-80 kVp, 5 to 500 μA max. For the CT experiments, the source was operated at 64 kVp, 400 μA or ~25 Watts. A 1 mm thick Al was used to filter the low energy x-ray component from the emerging beam. The estimated x-ray dose for the entire 360° scan was 5 cGy. It should be noted that this dose is a factor of 3 less compared to what is used in a normal scan using the ImTek microCAT system.

During data acquisition the object was continuously irradiated throughout the length of the scan without the use of a shutter. This was possible due to the very high rate of 'on-chip' data transfer offered by the CCD architecture (frame transfer mode), which minimizes any significant image blurring.

Figure 16:
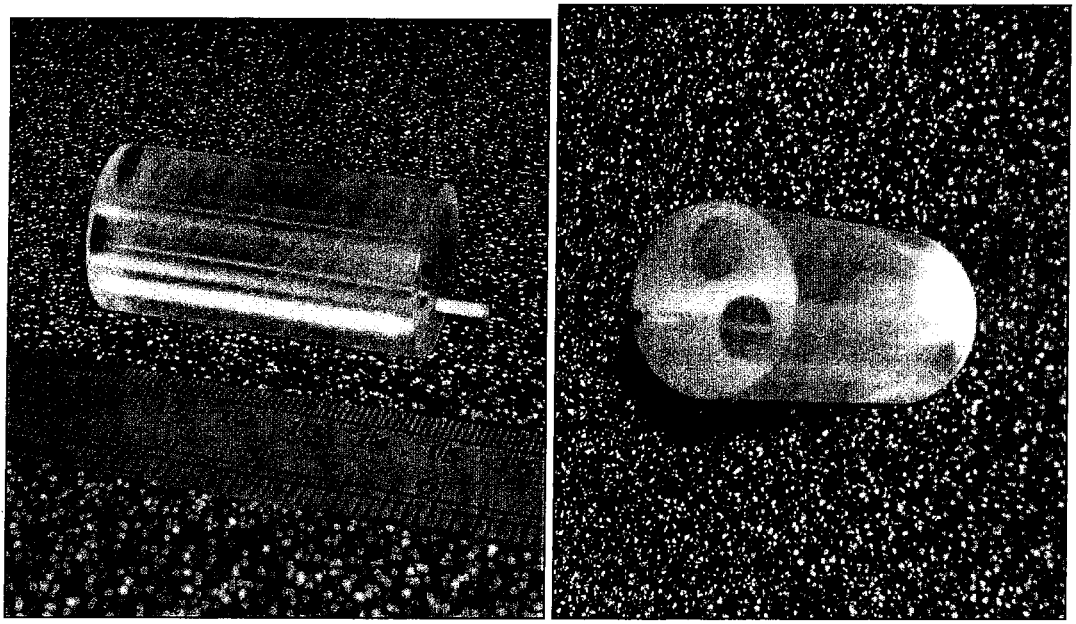
FIG. 16 illustrates a mouse phantom used as an object for high speed CT imaging.

A 'mouse' phantom comprising a ~2.5 cm diameter, 5 cm long Lucite cylinder with two ~1 cm diameter holes representing mouse lungs, and a 3 mm diameter hole fitted with a bone equivalent material representing the mouse spine was used. The Lucite itself is considered to be a tissue equivalent material. FIG. 16 shows photographs of the mouse phantom.

Three screens were tested during these experiments. A 230 μm (94 mg/cm$^2$) thick microcolumnar CsI(Tl) screen, a 130 mg/cm$^2$ GOS(Pr) screen and a 34 mg/cm$^2$ Kodak® Min-R 2000 screen. The Kodak® Min-R2000 screen was used for comparison as this is the screen currently used in the ImTek commercial small animal CT system. For each screen, three data sets were acquired by operating the camera at 30, 50, and 120 fps. A set of 100 dark and 100 flood images were acquired for flat field correction at each speed.

Figure 17:
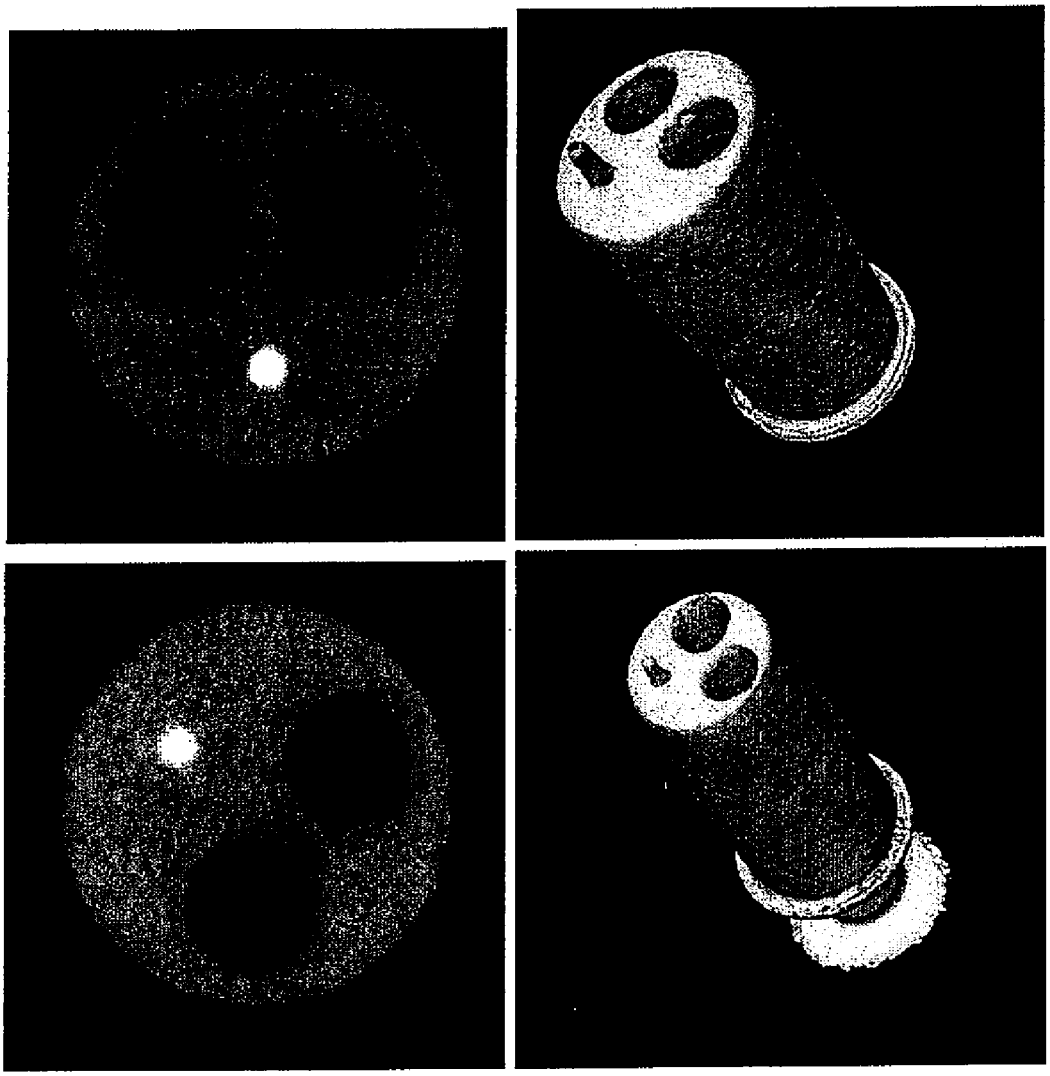
FIG. 17 illustrates a reconstructed mouse phantom using (a) CsI(Tl) screen and (b) GOS(Tb) screen. The data were acquired in 12.4 seconds and the projection images were captured at 30 fps. Compared to 300 second acquisition time required for the conventional systems, this shows a factor of 25 improvement in speed. This allows the use of the disclosed system for functional CT imaging.
Figures 20A, 20B, 20C, 20D:
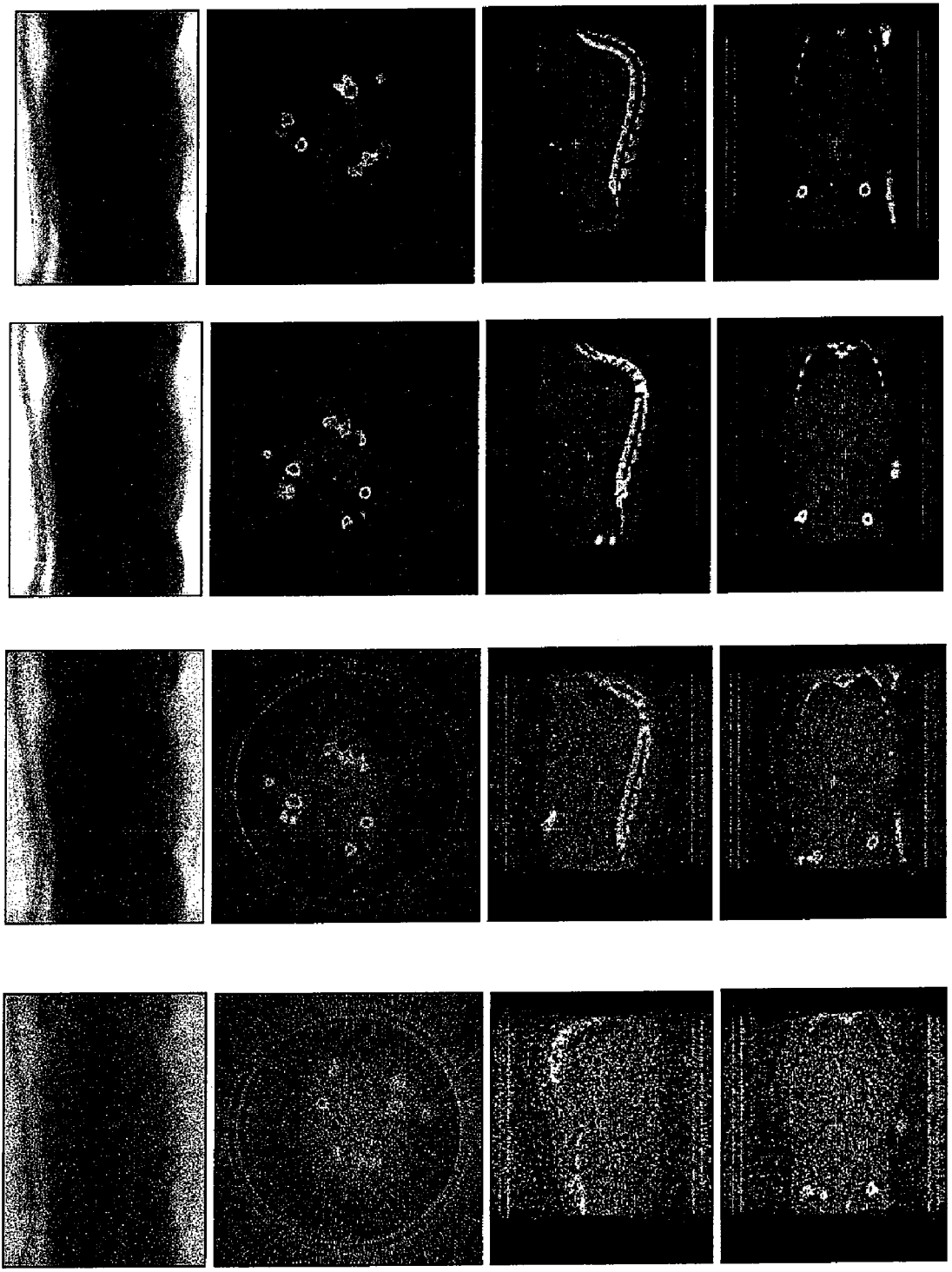
FIG. 20(a) through 20(d) provides radiographic projections and reconstructed images of euthanized mice obtained using the 150 μm CsI(Tl) screen at exposures listed in Table X.

The image data were converted to the standard ImTek format and reconstructed using the ImTek Feldkamp reconstruction algorithm. No corrections were introduced for lens distortion or bad CCD elements. The projection data has some "hot" CCD pixels generated by direct interaction of the x-ray photons with the silicon substrate of the CCD. No corrections were introduced to correct for these hot pixels and the dark streak artifacts in the images are attributed to these "hot" pixels. Improvements to this setup are to shield the detector from scattered radiation and to develop dynamic correction algorithms to remove these randomly occurring hot pixels. Images were viewed using the commercially available Amira™ software package. A two dimensional cross section and surface renderings of the data acquired using CsI(Tl) and GOS(Pr) at 30 fps are shown in FIG. 17. Note that the presence of thin adhesive tape on the mouse phantom is clearly resolved in the surface renderings.

It was possible to acquire good quality images at speeds up to 225 fps. Moreover, the system was successfully used to acquire a full set of cone beam CT on a mouse phantom in 12.4 seconds with only 5 cGy of x-ray dose. Conventional systems would typically require ~300-360 seconds for acquiring the same data set and would result in the x-ray dose of ~15 cGy. Thus, even the less than optimal system described above improved on the imaging speed by a factor of ~25, and on the dose by a factor of 3.

Preferred embodiments of the present invention use scintillator screens comprising a 7×7 cm active imaging area, and a 512×512 pixel resolution. Taking the magnification into account, the system provides ~90 μm of radiographic resolution. The x-ray detector is capable of acquiring images at the speed of up to 30 fps with 512×512 pixel resolution, and up to 300 fps with 512×32 pixel resolution. For a detector with 512 pixels, 804 projections are required for complete data sampling ($\{\pi/2\}$*Pixel elements). Thus, when operated at 300 fps, complete data sampling can be achieved in 2.7 seconds. The rotation stage can provide a maximum speed of 60 rpm or 1 second/rotation, which may be useful for phantom imaging. However, for small animal imaging it can be operated at adequately lower speeds (~6 seconds/rotation or grater) to minimize the physiological effects of spinning. The rotation time of 6 seconds permits acquisition of 180 frames or 1 frame/2' at 30 fps and 1800 frames or 5 frames/° at 300 fps. A system thus configured provides radiographic resolution of ~90 μm and a voxel resolution of ~100×100×100 μm$^3$ in the reconstructed data.

In one embodiment of the invention, the experimental data were acquired with a 512×512 pixel resolution, lens coupled, IGCCD detector configured to provide an ~13.8×13.8 cm$^2$ active image area. This resulted in a resolution of 270×270 μm in the detector plane. The configuration also resulted in a less than optimal optical coupling efficiency of ~0.07%. Consequently, the image quality suffered. The relatively poor image quality was a direct result of the geometry chosen for the experiment, and not a reflection of the IGCCD and CsI(Tl) scintillator combination. To confirm this, similar experiments have been subsequently carried out with a much more efficient geometry. As shown in Table VII, this configuration provided about 5×5$^{cm2}$ active image area with an effective resolution of approximately 100×100 μm$^2$ in the detector plane and an optical coupling efficiency of 0.45%. Thus, by sacrificing the active image area, we gained a factor of about 3 in spatial resolution and a factor of about 6 in coupling efficiency. The data presented here was obtained using this revised detector configuration.

TABLE VII

A comparison between detector configurations to demonstrate improved system geometry.

| Detector Configuration | Detector Field of View (cm$^2$) | IGCCD Size (cm$^2$) | Demagnification Ratio M | Lens F # | Lens Transmission T (%) | Effective Resolution (μm) | Coupling Efficiency g (%) |
|---|---|---|---|---|---|---|---|
| I | 13.8 × 13.8 | 0.82 × 0.82 | 16.8 | 0.95 | 80 | 270 | 0.07 |
| II | 5 × 5 | 0.82 × 0.82 | 6.1 | 0.95 | 80 | 97 | 0.45 |

In a series of test, the detector was evaluated in terms of response linearity as a function of x-ray exposure, as well as in terms of its overall imaging performance. The x-ray source used for these measurements was a Gendex Series 1000, tungsten target, 40-110 kVp continuously variable energy source set at 50 kVp. The source to detector distance was maintained at 65 cm. During each measurement the exposure was measured using Nuclear Associates Model 06-526-5280 Rad Check Exposure meter. The measurements were made using a 150 μm thick CsI(Tl) scintillator screen.

The linearity of system response was measured by exposing the detector to the flood field of 50 kVp x-rays. The x-ray exposure was varied over two orders of magnitude range by varying the data integration time. The choice of the exposure range was based on using the typical exposures in current small animal imaging and lowering it further by two orders of magnitude. In each case, dark images were subtracted from the flood field images and average signal in ADUs over the scintillator area and standard deviation of the signal was measured. The standard deviation was used to compute SNR at each exposure. FIG. 18 demonstrated the excellent detector response linearity over two orders of magnitude exposure range.

The system resolution was measured by imaging a Nuclear Associates line pair phantom Model No. 07-538, with 0.6 to 5.0 lp/mm bar pattern inscribed in lead. The phantom image was flat field corrected and contrast transfer function (CTF) was measured by computing modulation in a line profile taken through various bar patterns. Table VIII lists the resulting CTF values. It should be noted that although the 150 μm thick CsI(Tl) scintillator can resolve over 10 lp/mm, here the experiment was limited by the system Nyquist of 5 lp/mm.

TABLE VIII

Measured resolution of the system.

| lp/mm | 1 | 2 | 3 | 4 | 5 |
|---|---|---|---|---|---|
| CTF (%) | 85 | 60 | 35 | 18 | 8 |

The system contrast resolution as a function of x-ray exposure was measured by imaging the RMI, Inc. 118-step wedge phantom at various x-ray exposures. This aluminum phantom has five 3 mm steps. FIGS. 19(a) and 19(b) show images taken at 16 mR and 1 mR exposure. As expected, the quality of features in the image degraded with reduced exposure. The degradation in contrast (C) with reduced exposure was estimated to be only 30% by measuring the signal to background ratio for a given feature in the phantom. Table IX lists the resulting values of the contrast for 16 mR and 1 mR of exposure.

TABLE IX

Measured contrast transfer function of the system.

| | Step No. | | | | |
|---|---|---|---|---|---|
| | 1 | 2 | 3 | 4 | 5 |
| % contrast (C) 16 mR | 62 | 80 | 87 | 91 | 92 |
| % Contrast (C) 1 mR | 44 | 57 | 62 | 65 | 67 |

To demonstrate the feasibility of our approach, the components of the detector system was set up similarly to that show in FIGS. 15(a) and 15(b), and radiographic images of euthanized mice were recorded. This is a PC-based setup, with an x-ray tube and the digital detector controlled by data acquisition cards in the PC. The equipment was mounted on an optical breadboard to ensure stability and reproducibility. The one change from that shown in the figure was that the source to object and the object to detector distance was 17.5 cm each, resulting in an image magnification of 2. The x-ray exposure was controlled by a mechanical shutter moving in front of the x-ray tube and controlled by a stepper motor. For CT imaging, the object was placed on a rotating stage between the x-ray tube and the detector and was rotated to obtain the required number of views, typically in the range of 200 to 400.

The x-ray source used was an Oxford Instruments XRF-5011, 75 Watt, tungsten anode x-ray generator with a 70 μm focal spot. The output range on this source was 20-50 kVp, 1.5 mA max. A 1 mm thick Al sheet was used to filter the low energy x-ray component from the emerging beam. For the experiments reported here, the source was operated at 40 kVp, and the anode current was varied to vary the exposures. Exposures at the mouse location were measured using Inovision Radiation Measurements Model 350 50A ionization chamber. Various exposure settings used in these measurements and the percentage dose compared to that used in current imaging experiments are outlined in Table X.

TABLE X

Various exposure settings and the percentage dose compared to that used in current imaging experiments.

| kVp Setting | Tube Current (μm) | Exposure per projection (mR) | Integral dose for a 200 projection scan (cGy) | % Dose compared to current standard systems |
|---|---|---|---|---|
| 40 | 600 | 83.7 | 16.74 | 100% |
| 40 | 400 | 54.3 | 10.86 | 65% |
| 40 | 60 | 1.86 | 1.86 | 11% |
| 40 | 6 | 1.8 | 0.36 | 2% |

The radiographic projections and reconstructed images of euthanized mice obtained using the 150 μm thick CsI(Tl) screen at exposures listed in Table X are shown in FIG. 20(a) through 20(d). The reconstruction was performed using a conventional Feldkamp algorithm. In all 200 projections were acquired over 360° rotation, which resulted in an integral dose in the range of 0.3 to 16 cGy per scan. Since 15 cGy per scan is a typical dose to the mouse during a scan, the data acquired at 1.8 mR exposure per projection represented a factor of 50 lower dose than is conventionally used. Note that the images shown are raw images without flat field or any other correction. The projection data obtained at 83 mR dose show some "hot" pixels generated either by direct interaction of x-ray photons with the silicon substrate of the CCD or by the corona discharge in the gain register of the CCD87. No corrections were applied to eliminate these hot pixels. This problem will be minimized by use of a fiberoptic taper that will effectively attenuate x-rays that penetrate through the CsI(Tl) screen.

Although this detector suffered from sensitivity limitations, the reconstructed images show good resolution and contrast even for a total dose of <2 cGy. This was attributed to the excellent light conversion efficiency and spatial resolution of the microcolumnar CsI(Tl), and to the high SNR provided by the IGCCD due to its extremely low noise.

As can be seen from FIG. 20 (a) through 20(d) the image quality degraded with reduced exposure. This was to be expected as the detector, in its current configuration, is not x-ray photon limited. This was primarily due to the poor light coupling efficiency of the lens system, which was only 0.4%. Replacing the lens coupling with a more efficient fiberoptic taper coupling will enhance the efficiency by a factor of about 7 to 25 depending on the demagnification ratio of the taper used. Also, yet another factor of 3 gain in sensitivity will be achieved by using a back thinned IGCCD. Thus, the use of a fiberoptic taper along with a back-thinned CCD will improve the system sensitivity by a factor of 20 to approximately 75, and will correspondingly increase the SNR in the image. The use of tapers will also result in an improved resolution of 48 μm to 90 μm. This is a large gain in system performance and will allow achievement of higher values of detector DQE(f), and hence imaging at the reduced dose.

Modifications of the X-Ray Source

With the development of high-speed detector systems, scan time limitations will shift from the detector read-out rate to the available x-ray flux generated by the x-ray source. Traditionally, fixed anode mini-focus or micro-focus x-ray sources have been used in microCT systems due to their small focal spot size, reliability and ease of use. These are relatively low power units, however, with typical power ratings ranging from 10 to 75 W. In order to fully exploit the speed of the new CCD detector technology, the present invention may optionally employ a high-power mammography x-ray source.

Mammography sources typically employ rotating anodes and can operate at powers in excess of 1 kW. Mammographic x-ray source energies (15-25 keV) are somewhat low for laboratory mouse studies, but the higher operating power compensates for this deficiency. It is desirable to obtain a modified source with a Tungsten anode to increase the x-ray energy. Such a modified source has been used in the Fisher Imaging MammoScan full field mammography system. The typical focal spot rating for a mammographic x-ray source, 0.1 mm, is larger than that obtained with fixed anode sources. This increase in focal spot size will reduce the achievable resolution of the scanner. Because there is a desire to maximize the speed of whole-mouse tomographic scans, this compromise in resolution can at times be acceptable. In order to achieve the highest operating power, the x-ray source can be configured with a re-circulating cooling system and heat exchanger.

Advanced CT systems designed using the disclosed detector technology have far better temporal response than any system now in existence and allow functional whole organ imaging CT studies in small animals at much lower x-ray doses than currently used. The scanners of the present invention are capable of imaging tumor physiology in mice and other small animals. A functional microCT provides an improved approach for longitudinal high-resolution investigations of new anti-angiogenic therapies by using perfusion imaging of a tumor. Moreover, investigations of stroke physiology and developing new therapeutic approaches for treatment of acute cerebral ischemia will largely benefit from the availability of a high resolution imaging modality with enough active imaging area to cover the whole organ.

The detectors of the present invention allow tomographic imaging of a whole organ or tissue of interest with isotropic voxels. Also, it improves the spatial resolution by decreasing the voxel size from the current $0.3 \times 0.3 \times 1.25$ mm$^3$ to $<0.1 \times 0.1 \times 0.1$ mm$^3$. One desirable aspect of the detector of the present invention is its speed of operation, which allows the repeated acquisition of high resolution images over time, facilitating high resolution functional microCT studies of small animal physiology. This will substantially improve the accuracy of the quantification of physiologic parameters, such as blood flow (BF), blood volume (BV), transcapillary transfer constants (K1, k2), extraction fraction (E), and permeability surface area product (PS). With its large active area and high speed of operation, the detectors of the present invention allow for high-speed data acquisition through a whole organ such as, for example, the brain, lungs, heart, liver, and the like, enabling construction of temporal curves of the contrast passage for each individual voxel.

In the studies of tumor vascular physiology and angiogenesis it is desirable to be able to resolve the tumor vascular physiology with high resolution as tumors are known to be heterogeneous. With the high resolution and high speed provided by the detectors of the present invention, it is possible to investigate the heterogeneity of a tumor. This improves the assessment of the effects of new anti-angiogenic drugs that are currently under development.

Advantageously, the present invention may be scaled to perform human studies benefiting patient management in the future. The benefits of developing a functional microCT scanner are not limited to basic research and small animal studies. Ultimately, it may be possible to scale-up the concepts of the present invention for clinical patient studies for measurement of tissue vascular physiologic functions. A special CCD with higher pixel resolution (preferably 2K×2K or greater), larger pixel size (for improved sensitivity) will be needed. Also, a x-ray converter screen having high quantum efficiency with high light output will likely need to be used to maintain the high detector DQE(f) for fast readouts.

As these parameters are equally applicable for the detectors disclosed herein, successful development of the present detector may permit its use in human studies, and may promote the clinical use of physiologic imaging in the evaluation and treatment of diverse disease states, which will be an important advancement in the diagnosis, management and treatment of many significant diseases.

The detectors of the present invention may allow vascular physiology imaging so as to provide earlier and more specific diagnostic information related to heart attacks, cancer, and stroke. Outside the field of medicine, the detector of the present invention has further potential application in the areas of nondestructive testing (NDT), structural biology, x-ray astronomy, and basic research. For example, the NDT community needs a high-resolution fast detector for volumetric CT as well as radiographic scanning of adhesive bonded composites during the manufacturing process. As these components are used in aircraft and combat helicopters (e.g., V-22 Osprey), any integrity reducing anomalies must be removed before cure of the composite to ensure reliable operation, to reduce waste, and to minimize fabrication costs.

Simultaneous PET/CT Detector System

Figure 21:
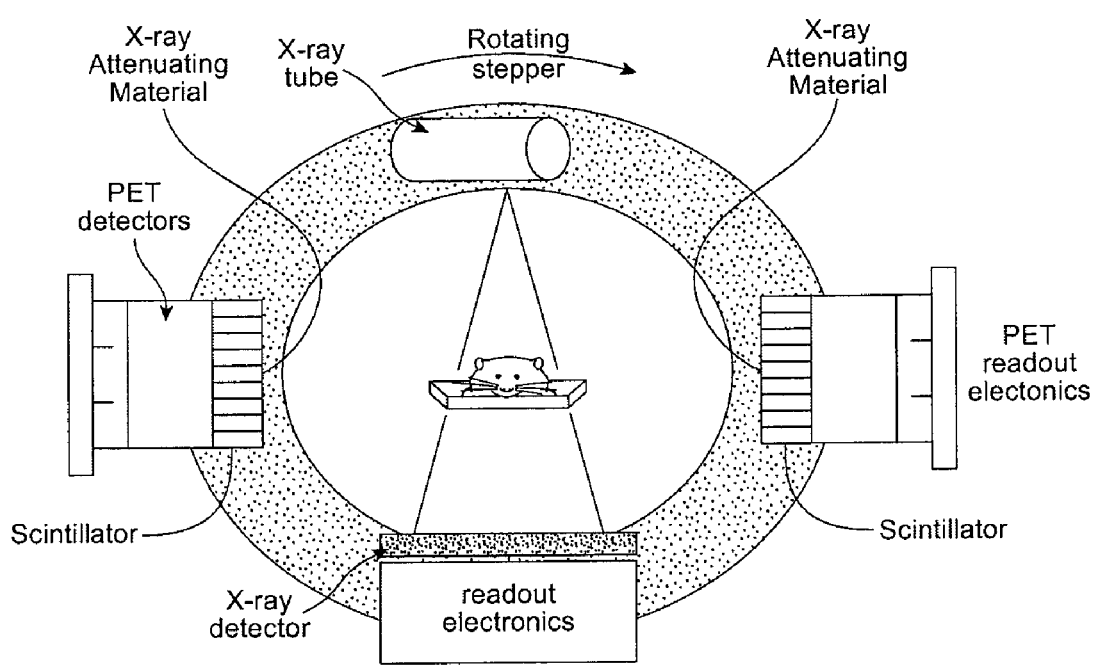
FIG. 21 provides a schematic of a combined PET/CT embodiment of the invention.

For simultaneous scanning of PET/CT data, both PET and CT detectors are mounted on the same gantry. This arrangement is shown schematically in FIG. 21. The PET detectors will consist of two planar panels of 0.95×0.95×12.5 mm3 LSO crystals directly coupled to an array of Hamamatsu RS900-M64 multichannel PMTs, or R7600 flat panel PMTs. Details of the PET part of the system are published and will not be discussed here in detail. A thin (1 mm) sheet of copper is placed in front of the PET detectors to shield them from x-rays scattered from the object. This eliminates x-ray flux on the PET detectors and only attenuates the 511 keV PET signal by about 3%.

A vertical rotating gantry allows the mouse to be stationary in the horizontal plane for imaging. The existing gantry consist of a ⅜" thick aluminum plate onto which a stepper motor rotational stage is mounted. This stage has <0.002 degree positional accuracy and is controlled using LabWindows/

CVI in a Windows NT environment. The gantry operates in step and shoot mode and is flexible enough to allow mounting of different types of detectors and x-ray tubes. It is capable of a single rotation through 360° to collect a full angular set of projection data. The radial location of the various components is variable, allowing the detector separation (PET) and the tube to detector distance (CT) to be adjusted in the range of 10 to 20 cm. As pointed out before, the field of view of the CT system will be approximately 48 mm in both transaxial direction and in the axial direction. The corresponding field of view of the PET system will be 50 mm in both directions.

Data from the PET detectors will be read out through position-encoding charge division schemes. Events that meet the energy criteria (typically 250-650 keV window) will be binned into sinograms (with appropriate correction for decay of the radionuclide) that will then be reconstructed using standard 3-D filtered backprojection techniques, or by Fourier rebinning techniques followed by 2-D OSEM reconstruction. Basic image display and image fusion software will be available on a host computer. The images will be written out in a straight binary format so they can easily be imported to other image analysis software for image manipulation and region of interest analysis. Although the foregoing invention has been described in detail for purposes of clarity of understanding, it will be obvious that certain modifications may be practiced within the scope of the appended claims.

What is claimed is:

1. A method of performing high speed, high resolution computed tomography (CT) imaging, comprising:
   providing a CT scanner assembly comprising an internal gain charge-coupled device (CCD) detector operatively coupled to a scintillation screen by an optical coupling path, and only a single x-ray source; and
   scanning a subject using the assembly so as to generate image data of a volume of the subject at an image acquisition rate of at least 30 frames per second, the image data comprising data having an image spatial resolution with a value of 100 µm or smaller.

2. The method of claim 1, wherein the imaging comprises holding the scanner assembly stationary while rotating the subject about the assembly.

3. The method of claim 1, wherein the imaging comprises holding the subject stationary while rotating the scanner assembly about the subject.

4. The method of claim 1, wherein the imaging comprises holding the subject and the assembly stationary while rotating the x-ray source about the subject.

5. The method of claim 1, wherein the CT scanner assembly is a microCT scanner assembly.

6. The method of claim 1, wherein the scintillation screen comprises a microcolumnar CsI(Tl) scintillator.

7. The method of claim 1, wherein the image acquisition rate is at least frames per second.

8. The method of claim 1, wherein the image acquisition rate is up to about 300 frames per second.

9. The method of claim 1, wherein the image data comprises data having an image spatial resolution with a value from about 50 µm to about 70 µm.

10. The method of claim 1, wherein the optical coupling path comprises a lens or fiber optic coupling.

11. The method of claim 1, wherein the imaging comprises functional imaging of dynamic small animal physiology.

12. The method of claim 1, wherein the imaging comprises perfusion imaging of a small animal tumor.

13. The method of claim 1, wherein the imaging comprises imaging of small animal stroke physiology.

14. The method of claim 1, wherein the imaging comprises imaging of small animal myocardial ischemia or infarction.

15. The method of claim 1, wherein the imaging comprises small animal imaging for cardiac functional analysis.

16. The method of claim 1, wherein the imaging comprises imaging with a liposomal CT contrast agent.

17. A method of performing high speed, high resolution computed tomography (CT) imaging of a volume of a subject, comprising:
   providing a high speed, microCT scanner assembly comprising an internal gain charge-coupled device (CCD) detector operatively coupled to a microcolumnar CsI(Tl) scintillation screen by an optical coupling path, and only a single x-ray source; and
   scanning a subject so as to generate image data of a volume of the subject at an image acquisition rate of at least 30 frames per second, the image data having an image spatial resolution with a value of 100 µm or smaller.

* * * * *